United States Patent [19]

Vlassara et al.

[11] Patent Number: 5,316,754
[45] Date of Patent: May 31, 1994

[54] IN VITRO ASSAY OF MESANGIAL CELL-DERIVED RECEPTORS FOR ADVANCED GLYCOSYLATION ENDPRODUCTS

[75] Inventors: Helen Vlassara, New York; Anthony Cerami, Shelter Island, both of N.Y.

[73] Assignee: The Rockefeller University, New York, N.Y.

[21] Appl. No.: 10,268

[22] Filed: Jan. 28, 1993

Related U.S. Application Data

[60] Division of Ser. No. 749,444, Aug. 23, 1991, Pat. No. 5,202,424, which is a continuation-in-part of Ser. No. 453,958, Dec. 20, 1989, abandoned, which is a division of Ser. No. 91,534, Sep. 3, 1987, Pat. No. 4,900,747, which is a continuation-in-part of Ser. No. 907,747, Sep. 12, 1986, abandoned, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.$^5$ .......................... C07K 3/00; C12Q 1/00; A01N 37/52; A61K 31/155
[52] U.S. Cl. .......................... 424/2; 424/9; 435/7.1; 435/7.9; 435/3; 435/4; 435/30; 435/240.2; 530/350; 530/380; 530/395; 530/397; 530/398; 530/399
[58] Field of Search .......................... 435/7.1, 7.9, 7.92, 435/7.93, 7.94, 240.2, 2, 3, 4, 20, 30, 40; 536/18.7; 514/402, 635; 424/2, 9; 530/395, 396, 397, 398, 399, 380

[56] References Cited

PUBLICATIONS

Vlassara et al. (1985) PNAS vol. 82:pp. 5588-5592.
Skolnik, E. et al, J. Exp. Med 174:931-939 (Oct., 1991).
Vlassara, H. et al, Science (Washington, D.C.) 240:1546-1548 (1988).
Esposito, C. et al. J. Exp. Med 170:1387-1407 (1989).
Schlondorf, D. J. Fed. Am. Soc. Exp. Biol. 1:272-281 (1987).
Lovett, D. H. et al., Kidney Int. 30/246-254 (1986).

*Primary Examiner*—Robert J. Hill, Jr.
*Assistant Examiner*—Gian P. Wang
*Attorney, Agent, or Firm*—Klauber & Jackson

[57] ABSTRACT

The present invention relates to a method and associated agents for measuring the presence and amount of advanced glycosylation endproducts in cells and fluids. The methods take advantage of the existence of receptors and receptor complexes for AGEs and include receptor-containing ligands comprising whole mesangial and other cells, mesangial cellular fragments and protein extracts therefrom. Competitive assays, sandwich assays and assays involving AGE antisera are disclosed. Numerous diagnostic applications are defined and test kits are also contemplated.

28 Claims, 10 Drawing Sheets

FIG. 6A
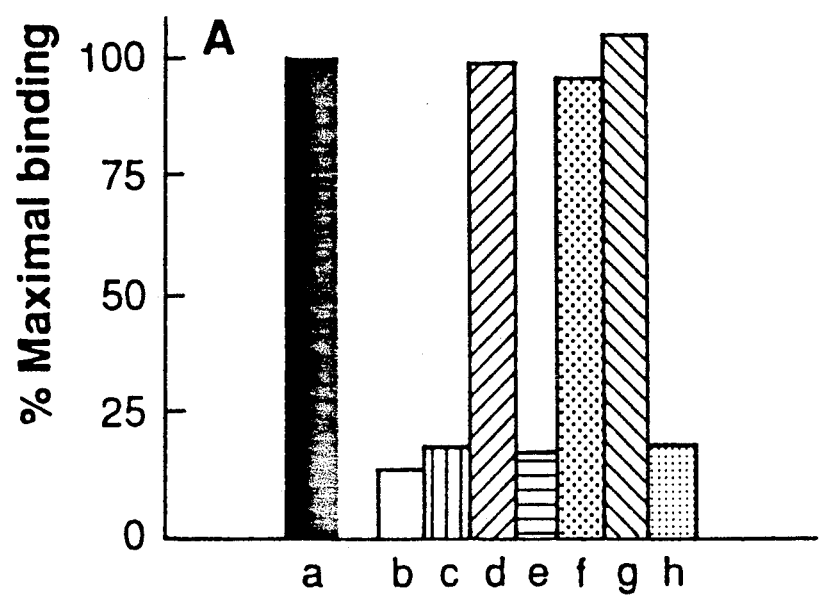
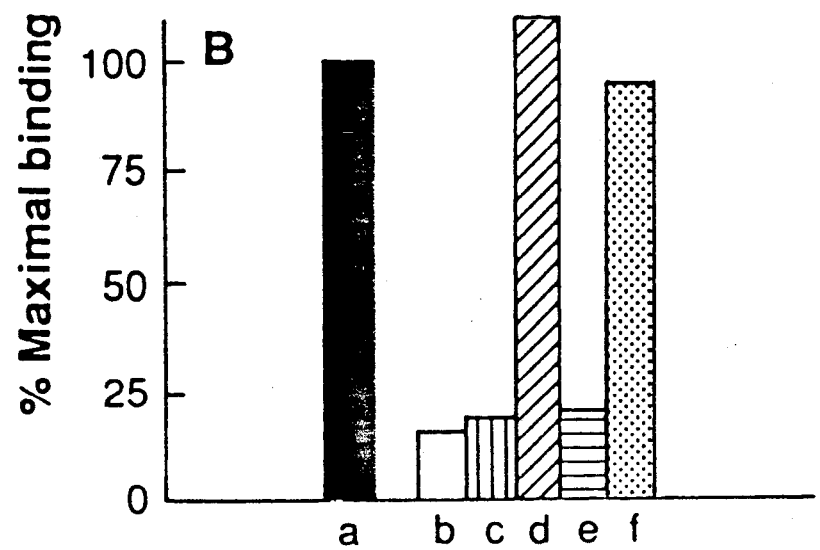
FIG. 6B

FIG. 7A
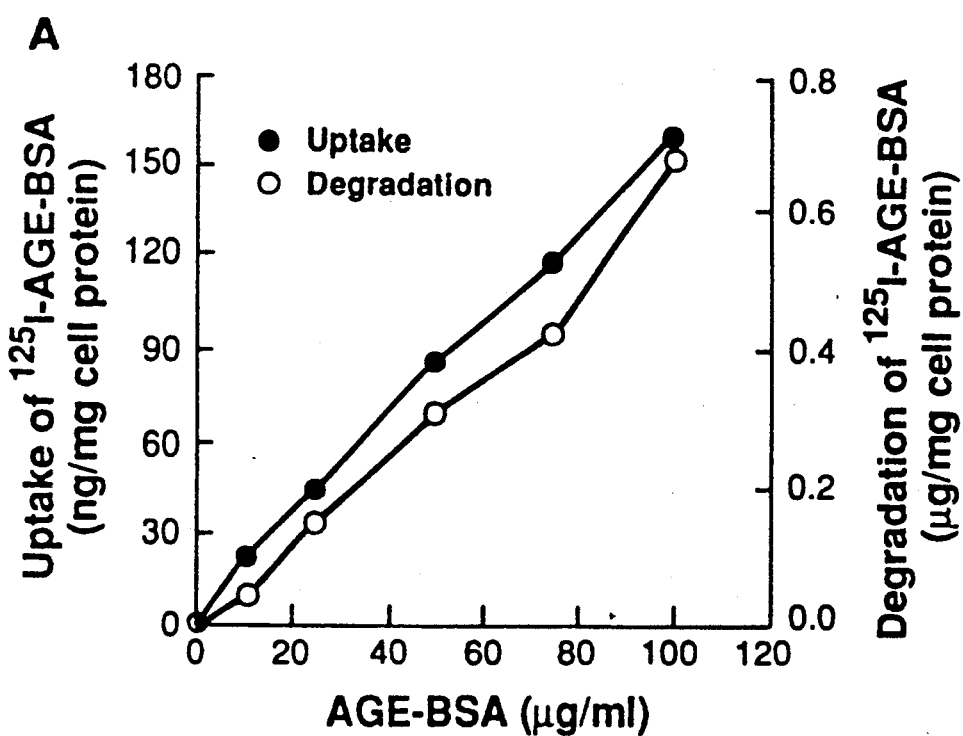
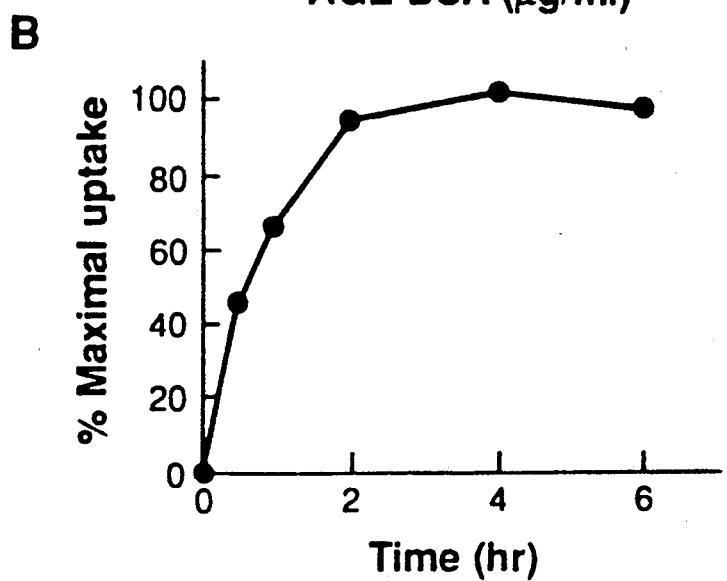
FIG. 7B

FIG. 10A
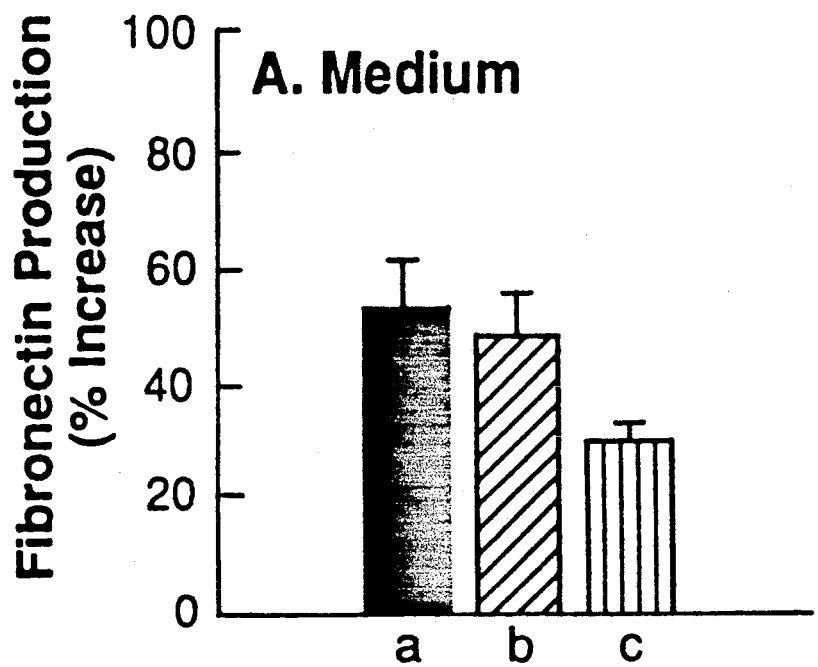
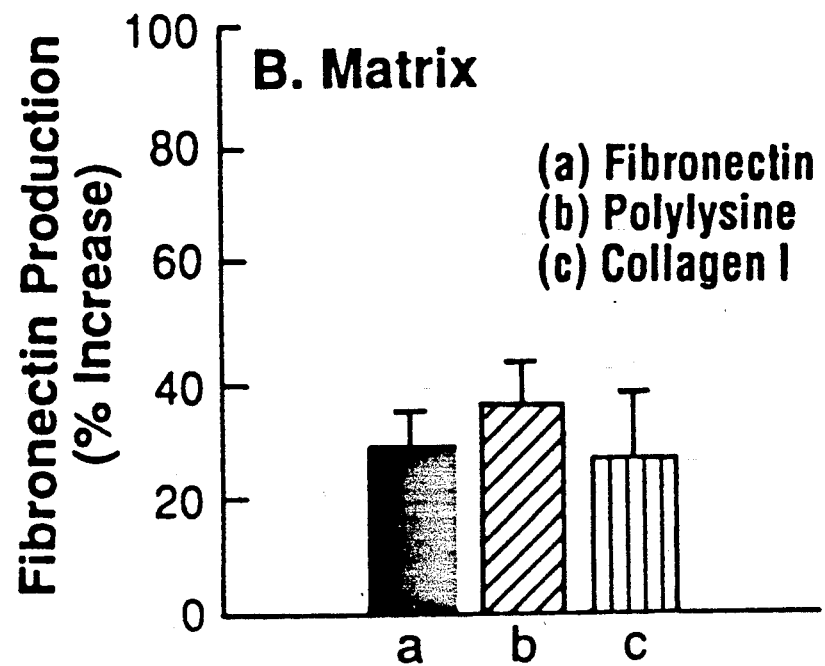
FIG. 10B

IN VITRO ASSAY OF MESANGIAL CELL-DERIVED RECEPTORS FOR ADVANCED GLYCOSYLATION ENDPRODUCTS

This invention was made with partial assistance from grant Nos. AG 8245 and DK 19655 from the National Institutes of Health. The government may have certain rights in this invention.

CROSS-REFERENCE TO RELATED APPLICATIONS

The present application is a division of application Ser. No. 07/749,444, filed Aug. 23, 1991, now U.S. Pat. No. 5,202,424, issued Apr. 13, 1993, which is a continuation in part of application Ser. No. 453,958, filed Dec. 20, 1989, abandoned which is in turn, a division of application Ser. No. 091,534, filed Sep. 3, 1987, now U.S. Pat. No. 4,900,747, issued Feb. 13, 1990, which is in turn, a continuation in part of application Ser. No. 907,747, filed Sep. 12, 1986, now abandoned; all of the above preceding applications by Helen Vlassara, Michael Brownlee and Anthony Cerami, said Ser. No. 907,747, in turn, a continuation in part of application Ser. No. 798,032, filed Nov. 14, 1985, by Anthony Cerami, Peter Ulrich and Michael Brownlee, now U.S. Pat. No. 4,758,583, which is, in turn, a continuation in part of application Ser. No. 590,820, now U.S. Pat. No. 4,665,192, filed Mar. 19, 1984 by Anthony Cerami alone.

Priority under 35 U.S.C. §120 is claimed as to all of the above earlier filed Applications, and the disclosures thereof are incorporated herein by reference.

RELATED PUBLICATIONS

The Applicants are co-authors of the following articles directed to the subject matter of the present invention: "FUNCTION OF MACROPHAGE RECEPTOR FOR NONENZYMATICALLY GLYCOSYLATED PROTEINS IS MODULATED BY INSULIN LEVELS", Vlassara, Brownlee and Cerami, DIABETES (1986), Vol. 35 Supp. 1, Page 13a; "ACCUMULATION OF DIABETIC RAT PERIPHERAL NERVE MYELIN BY MACROPHAGES INCREASES WITH THE PRESENCE OF ADVANCED GLYCOSYLATION ENDPRODUCTS", Vlassara, H., Brownlee, M., and Cerami, A. J. EXP. MED. (1984), Vol. 160, pp. 197-207; "RECOGNITION AND UPTAKE OF HUMAN DIABETIC PERIPHERAL NERVE MYELIN BY MACROPHAGES", Vlassara, H., Brownlee, M., and Cerami, A. DIABETES (1985), Vol. 34, No. 6, pp. 553-557; "HIGH-AFFINITY-RECEPTOR-MEDIATED UPTAKE AND DEGRADATION OF GLUCOSE-MODIFIED PROTEINS: A POTENTIAL MECHANISM FOR THE REMOVAL OF SENESCENT MACROMOLECULES", Vlassara H., Brownlee, M., and Cerami, A., PROC. NATL. ACAD. SCI. U.S.A. (September 1985), Vol. 82, pp. 5588-5592; "NOVEL MACROPHAGE RECEPTOR FOR GLUCOSE-MODIFIED PROTEINS IS DISTINCT FROM PREVIOUSLY DESCRIBED SCAVENGER RECEPTORS", Vlassara, H., Brownlee, M., and Cerami, A. JOUR. EXP. MED. (1986), Vol. 164, pp. 1301-1309; "ROLE OF NONENZYMATIC GLYCOSYLATION IN ATHEROGENESIS", Cerami, A., Vlassara, H., and Brownlee, M., JOURNAL OF CELLULAR BIOCHEMISTRY (1986), Vol. 30, pp. 111-120; "CHARACTERIZATION OF A SOLUBILIZED CELL SURFACE BINDING PROTEIN ON MACROPHAGES SPECIFIC FOR PROTEINS MODIFIED NONENZYMATICALLY BY ADVANCED GLYCOSYLATION END PRODUCTS", Radoff, S., Vlassara, H. and Cerami, A., ARCH. BIOCHEM. BIOPHYS (1988), Vol. 263, No. 2, pp. 418-423; "ISOLATION OF A SURFACE BINDING PROTEIN SPECIFIC FOR ADVANCED GLYCOSYLATION ENDPRODUCTS FROM THE MURINE MACROPHAGE-DERIVED CELL LINE RAW 264.7", Radoff, S., Vlassara, H., and Cerami, A., DIABETES, (1990), Vol. 39, pp. 1510-1518; "TWO NOVEL RAT LIVER MEMBRANE PROTEINS THAT BIND ADVANCED GLYCOSYLATION ENDPRODUCTS: RELATIONSHIP TO MACROPHAGE RECEPTOR FOR GLUCOSE-MODIFIED PROTEINS", Yang, Z., Makita, Z., Horii, Y., Brunelle, S., Cerami, A., Sehajpal, P., Suthanthiran, M. and Vlassara, H., J. EXP. MED., (In Press). All of the foregoing publications and all other references cited herein are incorporated by reference.

BACKGROUND OF THE INVENTION

The present invention relates generally to the nonenzymatic glycosylation of proteins, and particularly to the discovery of binding partners to advanced glycosylation endproducts such as AGE receptors, that may serve in the diagnosis and treatment of conditions in which the presence or activity of such advanced glycosylation endproducts may be implicated.

Glucose and other reducing sugars react nonenzymatically with the amino groups of proteins in a concentration-dependent manner. Over time, these initial Amadori adducts undergo further rearrangements, dehydrations and cross-linking with other proteins to accumulate as a family of complex structures which are referred to as Advanced Glycosylation Endproducts (AGEs). Although this chemistry has been studied by food chemists for many years, it was only in the past decade that the presence of AGEs in living tissue has been established. The excessive deposition of these products on structural proteins as a function of age and elevated glucose concentration, taken together with evidence of effective prevention of tissue pathology by an AGE inhibitor, aminoguanidine, has lent support to the hypothesis that the formation of AGEs plays a role in the long term complications of aging and diabetes.

Since the amount of AGEs found in human tissues is less than could be predicted from protein/glucose incubation studies in vitro, the applicants herein proposed several years ago that there might be normal mechanisms to remove those long-lived proteins which had accumulated AGEs in vivo. Particularly, and as set forth initially in Parent application Ser. No. 907,747, and the above-referenced applications that have followed, monocytes/macrophages and endothelial cells were found to display high affinity surface binding activity specific for AGE moieties independent of the protein which was AGE-modified. This AGE-receptor was shown to differ from other known scavenger receptors on these cells.

In addition, an endogenous means for the in vivo elimination or removal of advanced glycosylation endproducts was set forth, and corresponding diagnostic applications involving the receptors and including a specific receptor assay were also proposed.

Following this determination, the applicants herein have sought to further investigate the identity and role of advanced glycosylation endproduct receptors and possible binding partners, and any consequent diagnostic and therapeuptic implications of these investigations, and it is toward this end that the present invention is directed.

The AGE-specific receptor system now includes a variety of tissues and cell types in addition to monocyte/macrophages for which receptor-mediated AGE-protein internalization and digestion was first described. Endothelial, mesangial cells and fibroblasts have since been shown to specifically bind AGE-modified protein. In macrophages, AGE-protein uptake is accompanied by the release of a variety of potent cytokines and growth factors, which may coordinate processes of normal tissue remodeling. The other cell types do not bind the model compound AGE, FFI, nor are they known to release cytokines and growth factors in response to AGE-ligand binding, but each cell type does display distinct functional responses. For example, endothelial cells exhibit enhanced surface procoagulant activity and permeability; and mesangial cells display enhanced matrix protein synthesis; while human fibroblasts increase proliferation upon exposure to AGEs.

SUMMARY OF THE INVENTION

In accordance with the present invention, a substantially purified receptor as defined herein is disclosed that is derived from mammalian mesangial cells (MCs) that recognizes and binds advanced glycosylation endproducts. The receptor possesses the following characteristics:

A. It recognizes and binds with the ligands AGE-BSA, AGE-RNAse and AGE-collagen I in a saturable fashion, having a binding affinity of $2.0 \pm 0.4 \times 10^6 M^{-1}$ (500 nM);

B. It recognizes and binds to AGE-BSA which has been reduced with $NaBH_4$;

C. It does not recognize and bind with the ligand FFI-BSA, unmodified BSA, RNAse or collagen I in a solid phase ligand blotting assay; and D. It comprises one or more of at least three proteins, the first of said proteins having a molecular mass of about 50 kD, the second of said proteins having a molecular mass of about 40 kD and the third of said proteins having a molecular mass of about 30–35 kD, as determined by their migration on SDS-PAGE.

The present invention also includes various diagnostic and therapeutic utilities predicated on the identification and activities of the MC receptor for AGEs. Diagnostic utilities include assays such as immunoassays with labeled receptors, antibodies, ligands and binding partners, receptor assays, and screening assays to evaluate new drugs by their ability to promote or inhibit production or activity, as desired. The above assays can be used to detect the presence or activity of invasive stimuli, pathology or injury, the presence or absence of which may affect the structure or function of specific organs.

Therapeutic compositions comprising effective amounts of AGE receptor antagonists, agonists, antibodies or like drugs, etc., and pharmaceutically acceptable carriers are also contemplated. Such compositions can be prepared for a variety of protocols, including where appropriate, oral and parenteral administration. Exact dosage and dosing schedules are determined by the skilled physician.

The invention also includes a method for the measurement of protein aging both in plants and in animals, by assaying the presence, amount, location and effect of such advanced glycosylation endproducts. Assays of plant matter and animal food samples will be able, for example, to assess food spoilage and the degradation of other protein material so affected, while the assays of animals, including body fluids such as blood, plasma and urine, tissue samples, and biomolecules such as DNA, that are capable of undergoing advanced glycosylation, will assist in the detection of pathology or other systemic dysfunction.

Specifically, the methods comprise the performance of several assay protocols, involving the analyte, a ligand and one or more binding partners to the advanced glycosylation endproducts of interest. The binding partners may be selected from the group consisting of cells having receptors for advanced glycosylation endproducts, cell components having receptors for advanced glycosylation endproducts, cell proteins comprising receptors for advanced glycosylation endproducts, and antibodies to the advanced glycosylation endproducts, the receptors, cell components or cell proteins.

The preferred cells having receptors which are useful herein comprise mammalian mesangial cells; the preferred cellular components comprise cell membranes, and the cell proteins are derived from cell membranes and are selected from the group consisting of a 50 kD protein derived from MC membranes, a 40 kD protein derived from MC membranes, and a 30–35 kD protein derived from MC membranes, as well as mixtures thereof, having the reactivity which is described herein.

The ligands useful in the present invention are generally AGE derivatives that bind to AGE binding partners. These ligands may be detected either singly and directly, or in combination with a second detecting partner such as avidin. Suitable ligands are selected from the reaction products of reducing sugars, such as glucose and glucose-6-phosphate (G6P), fructose and ribose. These sugars are reactive with peptides, proteins and other biochemicals such as BSA, avidin, biotin, and enzymes such as alkaline phosphatase.

Included in this invention is the discovery and preparation of enzymes and other carriers that undergo advanced glycosylation and that may serve as labelled ligands in the assays of the present invention. Other suitable ligands may include synthetic AGEs or the reaction of the sugars directly with carriers capable of undergoing advanced glycosylation. Carriers not so capable may have a synthetic AGE coupled to them. Suitable carriers may comprise a material selected from carbohydrates, proteins, synthetic polypeptides, lipids, bio-compatible natural and synthetic resins, antigens and mixtures thereof.

Whole cell-based assays and standard assays based on either cell components or the cell proteins themselves and employing extracts may be used. The "whole cell" can be intact mesangial cells and/or other cells bound to ligands for the AGE receptors, such as labelled whole cells. Each assay is capable of being based on enzyme linked and/or radiolabeled AGEs and their binding partners, including the AGE receptors disclosed herein.

Assay Protocols

The broad format of the assay protocols possible with the present invention extends to assays wherein no label is needed for AGE detection. For example, one of the formats contemplates the use of a bound protein-specific AGE receptor. The analyte suspected of containing the advanced glycosylation endproducts under examination would need only to be added to the receptor. The bound analyte could then be easily detected by a change in the property of the binding partner, such as by changes in the receptor.

The assays of the invention may follow formats wherein either the ligand or the binding partner, be it a receptor or an antibody, are bound. Likewise, the assays include the use of labels which may be selected from radioactive elements, enzymes and chemicals that fluoresce.

The present method has particular therapeutic relevance as it affords a means for the detection and evaluation of the condition of a broad spectrum of organ systems. The Maillard process acutely affects several of the significant protein masses in the body, among them collagen, elastin, lens proteins, and the kidney glomerular basement membranes. These proteins deteriorate both with age (hence the application of the term "protein aging") and as a result of prolonged exposure to blood sugar and AGE formation, the latter in turn frequently due to pathology.

In this manner, the location and relative concentrations of advanced glycosylation endproducts in the body can be identified. This technique is particularly useful in identifying undesireable concentrations of advanced glycosylation endproducts, such as in atheromatous plaques. In such manner, the location of the systemic malfunction can be identified.

Accordingly, it is a principal object of the present invention to provide a method for measuring advanced glycosylation endproducts that is rapid and reliable.

It is a further object of the present invention to provide a method as aforesaid which is characterized by the discovery and use of the binding affinity of receptors for said advanced glycosylation endproducts.

It is a yet further object of the present invention to provide an assay for the measurement of advanced glycosylation endproducts that is capable of a broad range of alternative protocols.

It is a yet further object of the present invention to provide an assay as aforesaid that is capable of performance without radioactive labels and that may be performed in an automated fashion.

Other objects and advantages will become apparent to those skilled in the art from the teachings herein.

BRIEF DESCRIPTION OF THE DRAWINGS

The invention is described in detail in connection with the accompanying drawings, as set forth below.

FIGS. 6A-B—Competitive inhibition of $^{125}$I-AGE-BSA binding to human FIG. 6(A) and rat FIG. 6(B) MC membranes. 10 $\mu$g of solubilized membrane protein from human and rat MCs were dot-blotted onto nitrocellulose filters. The filters were incubated with 50 nM $^{125}$I-AGE-BSA for 2 hours at 4° C. Competition experiments were performed in parallel experiments in which the radioligand was incubated with 100-molar excess of an unlabeled protein. Data shown are the average of duplicate determinations, and are expressed as the % maximal binding. Maximal binding was defined as the amount of $^{125}$I-AGE-BSA bound in the presence of 100-molar excess cold BSA. Competitors used: (a) BSA, (b) AGE-BSA, (c) $NaBH_4$-reduced AGE-BSA, (d) FFI-BSA, (e) AGE-RNAse, (f) RNAse, (g) Collagen I, (h) AGE-collagen I.

FIGS. 7A-B—FIG. 7A) Uptake and degradation of $^{125}$I-AGE-BSA by rat MCs. MCs were incubated with various concentrations of $^{125}$I-AGE-BSA for 4 hours at 37° C. The amount of cell-associated $^{125}$I-AGE-BSA (uptake), and the amount of trichloroacetic acid-soluble counts in the medium (degradation) were determined in triplicate wells. FIG. 7B) Accumulation of $^{125}$I-AGE-BSA versus time. MCs in each well were incubated with 20 $\mu$g of $^{125}$I-AGE-BSA at 37° C. and specific cell-associated radioactivity was determined at various time intervals. Cellular accumulation of radioactivity is expressed as the % of the maximal accumulation of $^{125}$I-AGE-BSA.

FIGS. 10A-B—Effect of AGE-matrices on fibronectin synthesis by MCs. Human MCs were plated onto either unmodified or AGE-modified matrices and labeled with 35S-methionine and cysteine, as described. The amount of fibronectin released into the medium FIG. 10(A), and incorporated into the matrices FIG. 10(B), was determined by immunoprecipitation. The fibronectin bands on the gel were excised and counted for radioactivity. The values shown are expressed as the % increase in fibronectin produced by cells plated on the AGE-matrices relative to that produced by cells plated on control unmodified matrices. The values show cpm/well and represent the means±SEM from 4 experiments. a) Fibronectin, b) Polylysine, c) Collagen I.

DETAILED DESCRIPTION

Figure 1:
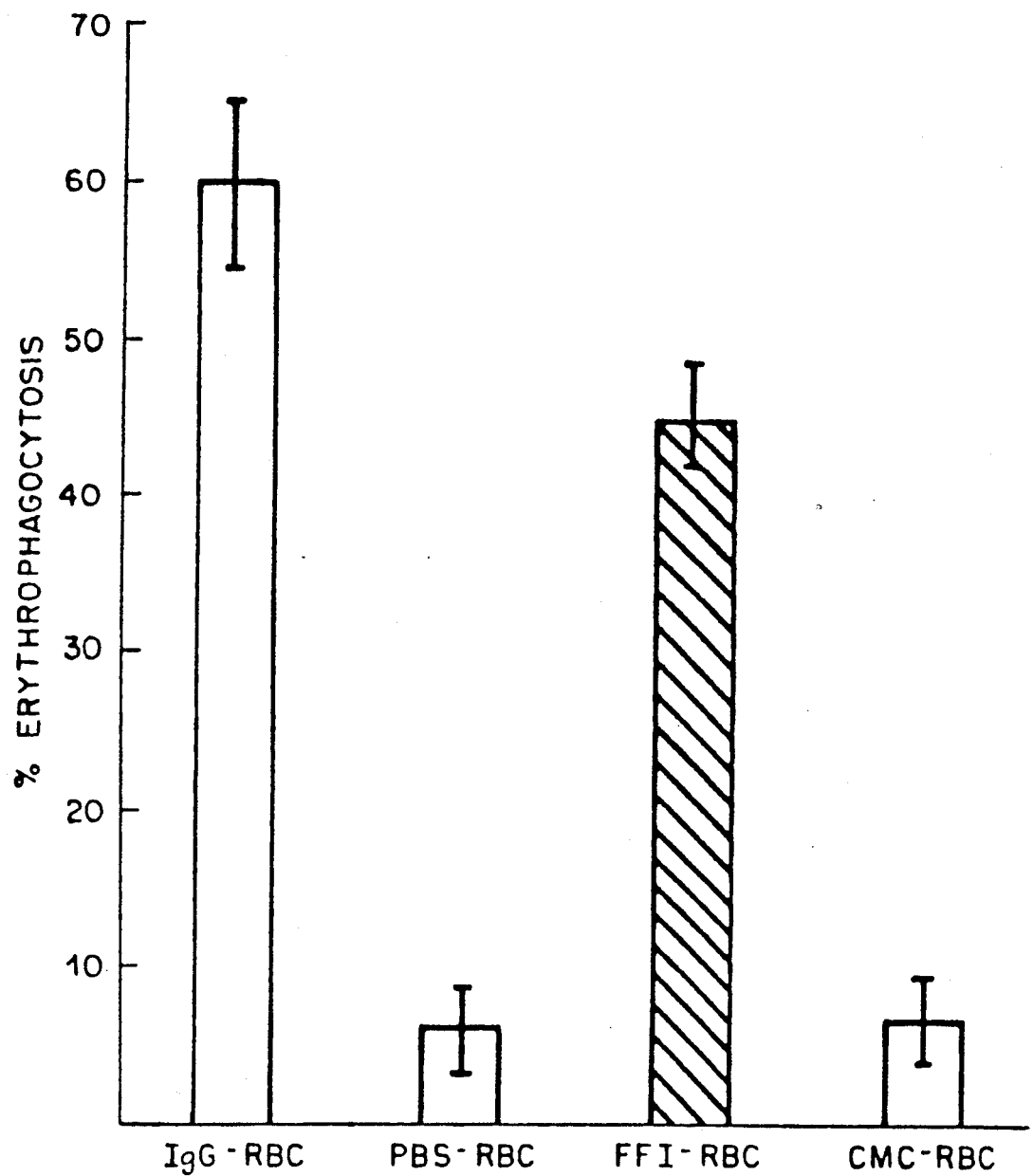
FIG. 1 is a graph depicting the relative binding and uptake of red blood cells modified with various agents, and illustrating a primary aspect of the present invention.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984).

As used herein, the term "AGE-" refers to the advanced glycosylation endproducts of the compound to which it relates. This compound is typically a protein having terminal amino groups which are reactive with reducing sugars. Examples include bovine endothelial ribonuclease (RNAse), human serum albumin (HSA), bovine serum albumin (BSA), collagen type (I) and other proteins.

As used throughout the present application, the term "receptor complex" includes both the singular and plural and contemplates the existence of a one or more receptor structures which are in turn comprised of the individual proteins defined herein.

The abbreviation "FFI" refers to the model AGE 2-(2-furoyl)-4(5)-(2-furanyl)-1H-imidazole, which can be reacted with a protein, e.g., BSA, by adding 100 mM carbodiimide to form the adduct FFI-BSA.

As noted above, the preferred cells containing AGE receptors are MCs. Mesangial cells are contained in the mammalian kidneys and function in conjunction with the glomeruli to regulate the glomerular filtration rate, thus affecting glomerular flow. Increases in the mesangial matrix have been shown to decrease the filtering surface of the glomerulus, and thus impinge upon the glomerular capillary vasculature. This is due to the accumulation of normal matrix proteins, e.g., collagen type IV, type V, laminin and fibronectin.

Mesangial cells have been evaluated as described herein, and found to contain AGE receptors. The specific findings that follow derive from the experiments the procedures of which are set forth in detail in Example 3, presented below. When AGE-modified proteins accumulate in the mesangial matrix and bind to these receptors, MC proliferation, synthesis, metabolism and physiology are modified. For example, the proliferation of MCs is reduced when AGEs have reacted with MC receptors as compared to MCs which have not been exposed to AGEs.

Additionally, when AGE-modified proteins are bound to MCs, an increase in fibronectin production is observed, which in turn causes an adverse build-up of the mesangial matrix.

The MC receptors which recognize AGEs are present on the cell membranes, and demonstrate binding to AGE-modified proteins in a saturable fashion with a binding affinity of about $2.0 \pm 04 \times 10^6$ $M^{-1}$ (kD=500 nM). This binding is specific for AGE-modified proteins; non-AGE modified proteins do not compete for receptor recognition in binding assays.

Figure 8:
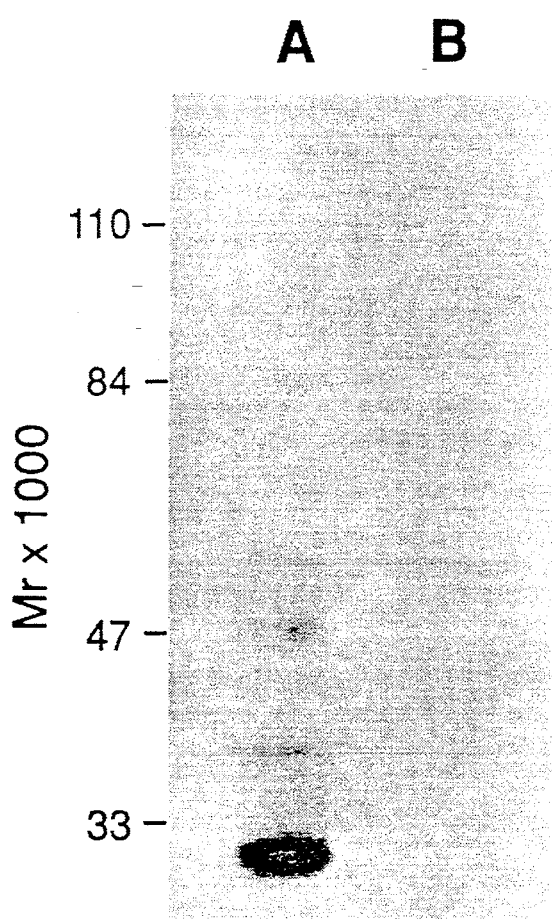
FIG. 8—Ligand blot analysis of enriched human MC membranes. 10 $\mu$g of solubilized membrane protein were electrophoresed on a nonreducing SDS/polyacrylamide gel (10%). The proteins on the gel were electroblotted onto nitrocellulose membrane and probed with $^{125}$I-AGE-BSA in the presence of 100-fold excess of either BSA (lane A) or AGE-BSA (lane B). The analysis presented is one of four identical experiments.

The MC receptors are comprised of at least 3 distinct proteins, 50 kD, 40 kD and 30–35 kD. This was demonstrated using a ligand blotting assay of MC membrane extracts, the procedure of which is described below. The results are shown in FIG. 8.

Figures 5A, 5B:
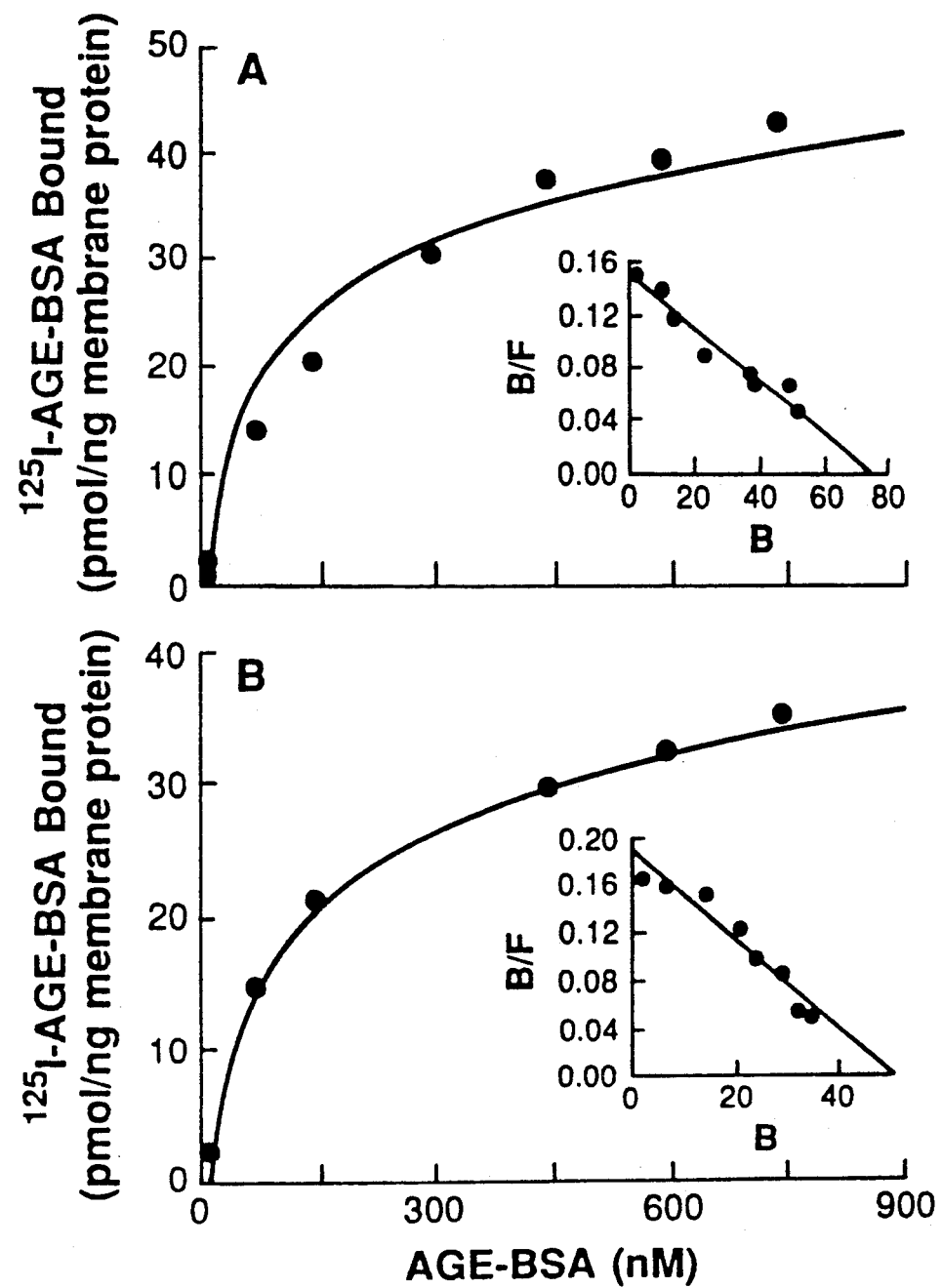
FIGS. 5A-B—Binding of $^{125}$I-AGE-BSA to human FIG. 5(A) and rat FIG. 5(B) MC membranes. 10 $\mu$g of solubilized membrane protein from human and rat mesangial cells were dot-blotted onto nitrocellulose filters, which were then incubated with various concentrations of $^{125}$I-AGE-BSA in the presence and absence of 100-fold excess unlabeled AGE-BSA. Specific binding was obtained by subtracting the nonspecific binding from the total binding. The inset shows a Scatchard Plot for the specific binding (B=pmoles/ng membrane protein, F=nM).

The MC AGE receptor was further characterized with respect to its binding affinity, using a series of assays. It was determined that the MC membrane AGE receptors bind AGEs in a saturable fashion. (See FIG. 5.) When MC membrane extracts were exposed to increasing levels of AGEs, specific binding plateaued, even as AGE levels were increased. Half-maximal binding occurred at about a 150nM concentration of AGE-BSA. This was consistent between rat and human MC membrane extracts. The number of AGE molecules bound per cell was in the range of $3.0 \pm 0.25 \times 10^5$ molecules per cell. The binding affinity constant was $2.0 \pm 0.40 \times 10^6$ $M^{-1}$ (kD=500nM).

Similar results were observed when whole MCs were assayed (data not shown).

The MC receptor binding affinity was further evaluated, and it was determined that the MC receptor for AGE-modified proteins is reactive with AGE-modified proteins and non-reactive with proteins in unmodified form. These conclusions were drawn based upon competitive binding assays run wherein the MC receptor for AGEs is dot-blotted onto a nitrocellulose filter, blocked with BSA, quantitated with labelled ligand and then competitive assayed with labelled ligand and the protein to be evaluated. Competition was evaluated based upon the level of reactivity, compared to that which was present when no competing protein was included.

Specific binding to the receptors was defined as the difference between total binding (radioligand incubated with membrane protein alone) and non-specific binding (cell incubated with radiolabelled ligand plus 100 fold excess of unlabelled ligand).

Scatchard analysis of the data was performed to determine the binding affinity constant and the receptor number. See Scatchard, G. Ann. N.Y. Acad. Sci. (1949) 51:660–72.

The competitive binding assays were run using rat and human MC extracts, with the results shown in FIG. 6. It was confirmed that AGE-modified proteins were binding to the receptors. Excess cold AGE-BSA (FIG. 6Ab, 6Bb) competed with labelled AGE-BSA. The excess cold AGE-BSA competitively inhibited greater than 80% of $^{125}$I-AGE-BSA binding to MC membrane extract, and other AGE-modified proteins, namely AGE-RNAse (FIG. 6Ae, 6Be), and AGE-collagen I (FIG. 6Ah) competed effectively with $^{125}$I-AGE-BSA.

Unmodified BSA (FIG. 6Aa, 6Ba) did not compete, nor did excess unmodified RNAse or collagen I (FIGS. 6Af, 6Bf and 6Ag).

The AGE-modified protein receptors were further characterized with respect to binding for AGE-BSA in reduced form. AGE-BSA was reduced with NaBH$_4$ to glucitolysine and further evaluated. The reduced AGE-BSA effectively competed with radiolabelled AGE-BSA for binding to MC membrane extracts (FIGS. 6Ac, 6Bc).

The chemically synthesized model AGE-, FFI was assessed for its competitive ability to bind to MC AGE-receptors. The results are shown in FIGS. 6Ad and 6Bd. It did not compete with labelled AGE-BSA. The MC receptor does not recognize FFI-BSA.

The characteristics of the MC AGE-modified protein receptor were evaluated to determine the number of proteins involved and their molecular weight. It was determined that three distinct membrane proteins are present in the receptor complex, 50 kD, 40 kD and 30-35 Kd, using a ligand blot analysis.

The receptor proteins were evaluated using detergent extracts of MC membranes. FIG. 8 shows three prominent AGE binding proteins. Binding of radiolabelled AGE to these membrane proteins was specific. Again, excess unlabelled AGE-BSA could inhibit labelled AGE-binding for both rat and human MCs, whereas BSA did not inhibit labelled AGE binding.

Figure 9:
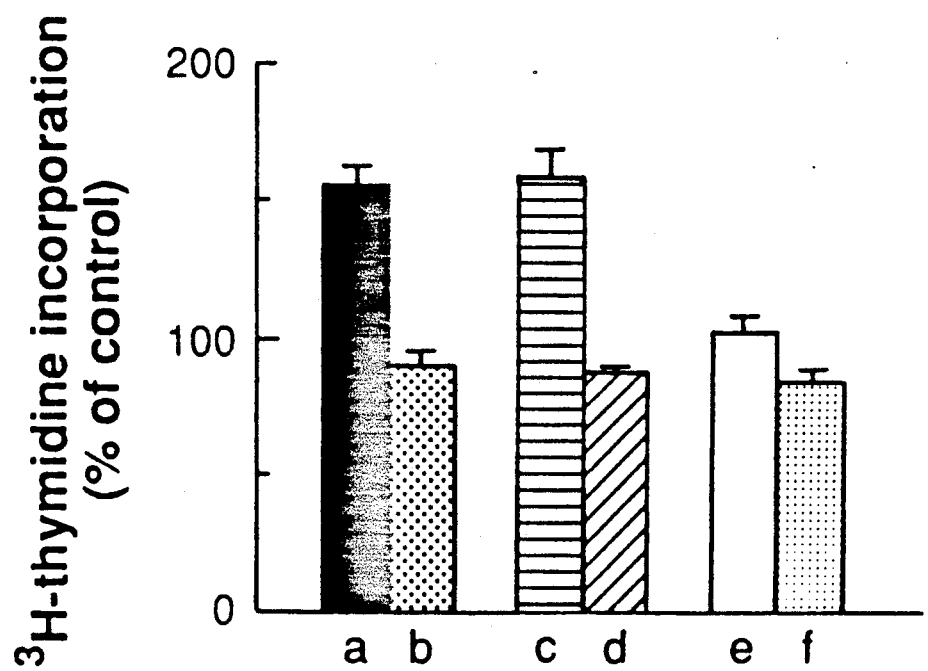
FIG. 9—Effects of AGE-matrices on [$^3$H]thymidine incorporation by MCs. Rat MCs were plated onto various matrices (10 $\mu$g/ml), as described: (a) Fibronectin, (b) AGE-Fibronectin, (c) Collagen I, (d) AGE-Collagen I, (e) Laminin, (f) AGE-Laminin. The results are expressed as the means±SEM of 6 experiments and are expressed as the % of [$^3$H]thymidine incorporated relative to the control value, with control representing [$^3$H]thymidine incorporated by cells plated on plastic.

The effect of AGEs on mesangial cell metabolism was evaluated using a number of different comparisons. Typically, the analysis addressed a particular metabolic parameter in AGE-modified MCs, and compared it to MCs unexposed to AGEs. To evaluate the effect of AGEs on MC proliferation, MCs were incubated with and without AGE-modified proteins in the presence of labelled thymidine. (Thymidine is taken up during DNA synthesis). The results are shown in FIG. 9. AGE-modified MCs showed a decrease in label uptake over MCs not exposed to AGEs.

MC proliferation was also evaluated in the presence of matrix proteins, fibronectin, collagen I and laminin, comparing MC growth on plates coated with these matrix proteins to that which occurs in the presence of these matrix proteins in AGE modified form. The results are shown in FIG. 9. Labelled thymidine uptake was used as the measure of MC proliferation. When used in a concentration of 10 mg/ml, the uptake of labelled thymidine uptake was consistently reduced in the presence of AGE-modified matrix proteins, approximately to the level of incorporation in MCs plated on plastic.

In contrast cells grown on collagen I and fibronectin coated plates (non-AGE modified) showed enhanced thymidine uptake; cells grown on non-AGE modified laminin coated plates showed no stimulated uptake over control values.

The reduced thymidine uptake in the presence of AGE modified fibronectin, collagen I and laminin was confirmed with Brd U incorporation assays used to control for DNA synthesis.

The uptake and degradation of AGEs by MCs was also evaluated using the procedures of Vlassara, H. et al. *Proc. Natl. Acad. Sci. USA* (1985); 82:5588-92 (modified slightly). MC accumulation of labelled ligand (AGE-BSA) was assessed by incubating cells with various concentrations of labelled AGE-BSA in the presence or absence of a 100 fold excess of unlabelled AGE-BSA. The amount of cell-contained label was determined. This is generally indicative of AGE uptake by MCs. The results are shown in FIGS. 7. Uptake data is shown in FIGS. 7A and 7B. MCs continued to accumulate AGEs beyond the level of AGE-binding to as high as 1.1 $\mu$M.

Since the level of AGE accumulation could include both bound AGEs and internalized AGEs, accumulation at 4° C. was compared to that at 37° C. (At 4° C. AGEs bind to MCs, whereas at 37° C. AGEs are internalized by MCs.) The maximum accumulation of labelled AGE-BSA occurred within 2 hours of incubation at 37° C. (FIG. 7B). The amount of label which was cell associated at 37° C. was 2-4 times higher than the amount of label bound to MCs at 4° C.

Degradation of AGEs was determined by measuring the amount of label present in the aspirated medium.

Concomitant with MC accumulation of labelled AGE-BSA, ligand degradation also increased, as measured by a steady increase in trichloroacetic acid (TCA) soluble radioactivity in the media. The increase in AGE-BSA degradation paralleled the increase in MC uptake of AGE-BSA. (FIG. 7A).

The effect of AGEs on fibronectin production in MCs was also evaluated. Mesangial cells were grown on AGE-modified or unmodified collagen I, fibronectin and polylysine media. The amount of fibronectin released into the medium (or incorporated into the matrix) was determined by immunoprecipitation with IgG purified anti-human fibronectin antibodies. The results are shown in FIG. 10, showing an increase in the synthesis of fibronectin in the presence of AGE-modified proteins.

The mesangial cells receptors for AGE- modified proteins can be further characterized by comparing said receptors to other known AGE-receptors, such as on macrophage and endothelial cells. AGEs have been shown to bind to specific receptors on murine and human monocyte/macrophages, as well as on bovine and human endothelial cells. Since AGEs form progressively over time, the function of AGE receptors is believed to include signalling cells to promote turnover of aging tissue. Under normal conditions, the removal of AGE- modified proteins occurs at a rate which keeps up with production, thereby preventing accumulation.

In diabetes, excessive AGE formation in the presence of elevated glucose levels results in a net increase of AGEs on most structural tisue proteins.

Macrophages are induced to release the cytokines catechin/tumor necrosis factor (TNF), interleukin-1 (IL-1), platelet derived growth factor (PDGF), and insulin-like growth factor (ILGF). Excessive blood glucose levels may lead to an exaggerated response, which could contribute to complications, e.g., atherosclerotic plaque formation, mesangial expansion and the like.

Endothelial cell AGE receptors induce several changes in EC function which are characteristic in diabetes, such as increased EC permeability and procoagulant properties.

The macrophage AGE receptors recognize the model AGE, FFI-BSA; in contrast, endothelial cell AGE receptors do not recognize the AGE- FFI-BSA.

The ability of MCs to slowly internalize and degrade AGE-modified proteins points to a contributing role for MCs in the turnover and remodeling of senescent AGE-modified mesangial matrix proteins. The efficiency with which MCs ingest and degrade AGE-BSA is approximately 10% of that which has been reported for the macrophage. While the AGE receptors on MCs, macrophage cells and endothelial cells all recognize AGEs to a degree, there are other differences. First, the Kds for the receptors are different. The Kd for macrophage and endothelial cell AGE receptors is about 70-100 nM; the Kd for MC AGE receptors is about 500 nM.

In addition, the efficiencies at which the AGE receptors from these three cell types internalize and degrade AGE-modified proteins are different. Macrophage AGE receptors ingest and degrade AGE-BSA at a much higher rate than do endothelial cells or MCs.

Lastly, macrophage AGE receptors recognize the specific adduct FFIO-BSA, whereas endothelial cell and MC AGE receptors do not. These differences in reactivity can be used to characterize the AGE receptor proteins derived from their respective cell types.

In accordance with the present invention, methods have been developed for the measurement of the presence and amount of advanced glycosylation endproducts in both plants and animals, including humans. The methods comprise assays involving in addition to the analyte, one or more binding partners of the advanced glycosylation endproducts, and one or more ligands.

Accordingly, the present assay method broadly comprises the steps of:

A. preparing at least one biological sample suspected of containing said advanced glycosylation endproducts;

B. preparing at least one corresponding binding partner directed to said samples;

C. placing a detectible label on a material selected from the group consisting of said samples, a ligand to said binding partner and said binding partner;

D. placing the labeled material from Step C in contact with a material selected from the group consisting of the material from Step C that is not labeled; and E. examining the resulting sample of Step D for the extent of binding of said labeled material to said unlabeled material.

Suitable analytes may be selected from plant matter, blood, plasma, urine, cerebrospinal fluid, lymphatic fluid, and tissue; and the compounds FFI and AFGP, individually and bound to carrier proteins such as the protein albumin. The analyte may also comprise a synthetically derived advanced glycosylation endproduct which is prepared, for example, by the reaction of a protein or other macromolecule with a sugar such as glucose, glucose-6-phosphate, or others. This reaction product could be used alone or could be combined with a carrier in the same fashion as the FFI-albumin complex.

The carrier may be selected from the group consisting of carbohydrates, proteins, synthetic polypeptides, lipids, bio-compatible natural and synthetic resins, antigens and mixtures thereof.

The present invention is also useful in diagnosing both the degradative effects of advanced glycosylation of proteins in plants and the like, and the adverse effects of the buildup of advanced glycosylation endproducts in animals. Such conditions as age-or diabetes-related hardening of the arteries, skin wrinkling, arterial blockage, and diabetic, retinal and renal damage in animals all result from the excessive buildup or trapping that occurs as advanced glycosylation endproducts increase in quantity. ,Therefore, the diagnostic method of the present invention is used to detect or avert pathologies caused at least in part by the accumulation of advanced glycosylation endproducts in the body by monitoring the amount and location of such AGEs.

Likewise, as advanced glycosylation endproducts may be measured by the extent that they bind to receptors on cells from a variety of sources, the assays of the present invention have been designed and may be performed around this activity. For example, in a typical competitive assay in accordance with the present invention, the receptor or cellular material bearing the receptor may be combined with the analyte and the ligand and the binding activity of either or both the ligand or the analyte to the receptor may then be measured to determine the extent and presence of the advanced glycosylation endproduct of interest. In this way, the differences in affinity between the components of the assay serves to identify the presence and amount of the AGE.

The present invention also relates to a method for detecting the presence of stimulated, spontaneous, or idiopathic pathological states in mammals, by measuring the corresponding presence of advanced glycosylation endproducts. More particularly, the activity of AGEs may be followed directly by assay techniques such as those discussed herein, through the use of an appropriately labeled quantity of at least one of the binding partners to AGEs as set forth herein. Alternately, AGEs can be used to raise binding partners or antagonists that could in turn, be labeled and introduced into a medium to test for the presence and amount of AGEs therein, and to thereby assess the state of the host from which the medium was drawn.

Thus, both AGE receptors and any binding partners thereto that may be prepared, are capable of use in connection with various diagnostic techniques, including immunoassays, such as a radioimmunoassay, using for example, a receptor or other ligand to an AGE that may either be unlabeled or if labeled, then by either radioactive addition, reduction with sodium borohydride, or radioiodination.

In an immunoassay, a control quantity of a binding partner to advanced glycosylation endproducts may be prepared and optionally labeled, such as with an enzyme, a compound that fluoresces and/or a radioactive element, and may then be introduced into a tissue or fluid sample of a mammal believed to be undergoing invasion. After the labeled material or its binding partner(s) has had an opportunity to react with sites within the sample, the resulting mass may be examined by known techniques, which may vary with the nature of the label attached.

The presence of AGE activity in animals and plants can be ascertained in general by immunological procedures are which utilize either a binding partner to the advanced glycosylation endproduct or a ligand thereto, optionally labeled with a detectable label, and further optionally including an antibody $Ab_1$ labeled with a detectable label, an antibody $Ab_2$ labeled with a detectable label, or a chemical conjugate with a binding partner to the advanced glycosylation endproduct labeled with a detectable label. The procedures may be summarized by the following equations wherein the asterisk indicates that the particle is labeled, and "R" in this instance stands for all binding partners of advanced glycosylation endproduct(s) under examination although particular reference is to be made to the receptor complex of the present invention:

A. $BP + Ab_1 = BP^*Ab_1$
B. $BP + Ab^* = BPAb_1^*$
C. $BP + Ab_1 + Ab_2^* = BPAb_1Ab_2^*$
D. Carrier $^*BP + Ab_1 =$ Carrier$^*BPAb_1$ These general procedures and their application are all familiar to those skilled in the art and are presented herein as illustrative and not restrictive of procedures that may be utilized within the scope of the present invention. The "competitive" procedure, Procedure A, is described in U.S. Pat. Nos. 3,654,090 and 3,850,752. Optional procedure C, the "sandwich" procedure, is described in U.S. Pat. Nos. RE 31,006 and 4,016,043, while optional procedure D is known as the "double antibody", or "DASP" procedure.

A further alternate diagnostic procedure employs multiple labeled compounds in a single solution for simultaneous radioimmune assay. In this procedure disclosed in U.S. Pat. No. 4,762,028 to Olson, a composition may be prepared with two or more analytes in a coordinated compound having the formula: radioisotope-chelator-analyte.

In each instance, the advanced glycoslation endproduct forms complexes with one or more binding partners and one member of the complex may be labeled with a detectable label. The fact that a complex has formed and, if desired, the amount thereof, can be determined by the known applicable detection methods.

With reference to the use of an AGE antibody as a binding partner, it will be seen from the above that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. Where used and for purposes of this description, $Ab_1$ will be referred to as a primary or anti-advanced glycosylation endproduct antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

Suitable radioactive elements may be selected from the group consisting of $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. In the instance where a radioactive label, such is prepared with one of the above isotopes is used, known currently available counting procedures may be utilized.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the advanced glycosylation endproducts, their binding partners or carrier molecules by reaction with bridging molecules such as carbodiimides, diisocyanates, glutaraldehyde and the like. Also, and in a particular embodiment of the present invention, the enzymes themselves may be modified into advanced glycosylation endproducts by reaction with sugars as set forth herein.

Many enzymes which can be used in these procedures are known and can be utilized. The preferred are peroxidase, $\beta$-glucuronidase, $\beta$-D-glucosidase, $\beta$-D-galactosidase, urease, glucose oxidase plus peroxidase, hexokinase plus GPDase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850,752; and 4,016,043 are referred to by way of example for their disclosure of alternative labeling material and methods.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The present invention includes assay systems that may be prepared in the form of test kits for the quantitative analysis of the extent of the presence of advanced glycosylation endproducts. The system or test kit may comprise a labeled component prepared by one of the radioactive and/or enzymatic techniques discussed herein, coupling a label to a binding partner to the advanced glycosylation endproduct such as a receptor or ligand as listed herein; and one or more additional immunochemical reagents, at least one of which is a free or immobilized ligand, capable either of binding with the labeled component, its binding partner, one of the components to be determined or their binding partner(s).

In a further embodiment of this invention, commercial test kits suitable for use by a medical specialist may be prepared to determine the presence or absence of advanced glycosylation endproducts. In accordance with the testing techniques discussed above, one class of such kits will contain at least labeled AGE, or its binding partner as stated above, and directions, of course, depending upon the method selected, e.g., "competitive", "sandwich", "DASP" and the like. The kits may also contain peripheral reagents such as buffers, stabilizers, etc.

For example, a first assay format contemplates a bound receptor to which are added the ligand and the analyte. The resulting substrate is then washed after which detection proceeds by the measurement of the amount of ligand bound to the receptor. A second format employs a bound ligand to which the receptor and the analyte are added. Both of the first two formats are based on a competitive reaction with the analyte, while a third format comprises a direct binding reaction between the analyte and a bound receptor. In this format a bound receptor-specific carrier or substrate is used. The analyte is first added after which the receptor is added, the substrate washed, and the amount of receptor bound to the substrate is measured.

More particularly, the present invention includes the following protocols within its scope:

I. A method for determining the amount of advanced glycosylation endproducts in an analyte comprising:

A. providing a sample of mesangial cells;

B. inoculating said sample with a known advanced glycosylation endproduct bound to a whole cell; and C. counting the whole cells of Step B that are bound to and/or internalized by said sample.

II. A method for determining the amount of advanced glycosylation endproducts in an analyte comprising:

A. providing a sample taken from mesangial cells believed to contain receptors for said advanced glycosylation endproducts;

B. incubating said sample with a radiolabeled complex of an advanced glycosylation endproduct and a protein; and C. detecting the radioactivity of said sample and counting the number of receptors thereon.

III. A method for determining the amount of advanced glycosylation endproducts in an analyte comprising:

A. providing a sample taken from mesangial cells modified to define receptors for advanced glycosylation endproducts;

B. incubating the sample of Step A with an analyte suspected of containing AGEs for a period of about 30 minutes;

C. applying a quantity of $^{125}$I-AGE-BSA to the sample of Step B with removal of any excess by rinsing; and D. measuring the amount of said advanced glycosylation endproduct bound to said analyte by detecting the radioactivity of the sample of Step C.

IV. A method for determining the amount of advanced glycosylation endproducts in an analyte comprising:

A. preparing a sample of said analyte by extraction from cellular components and blotting onto a suitable carrier or substrate;

B. incubating the sample after preparation in accordance with Step A, in a blocking buffer;

C. applying a quantity of $^{125}$I-AGE-BSA to the sample of Step B with removal of any excess by rinsing; and D. measuring the amount of said advanced glycosylation endproduct bound to said analyte by detecting the radioactivity of the sample of Step C.

V. A method for determining the amount of advanced glycosylation endproducts in an analyte comprising:

A. preparing a sample of said analyte bound to a substrate;

B. applying to the sample of Step A a quantity of a ligand bearing a known advanced glycosylation endproduct;

C. applying to the sample of Step B a quantity of an anti-serum to advanced glycosylation endproducts; and D. measuring the amount of said advanced glycosylation endproduct bound to said analyte by detecting the quantity of antiserum present on the bound substrate sample of Step C.

Each of the specific protocols set forth above is illustrated in the examples that follow herein, and reflects the broad latitude of the present invention. All of the protocols disclosed herein may be applied to the qualitative and quantitative determination of advanced glycosylation endproducts and to the concomitant diagnosis and surveillance of pathologies in which the accretion of advanced glycosylation endproducts is implicated. Such conditions as diabetes and the conditions associated with aging, such as atherosclerosis and skin wrinkling represent non-limiting examples, and accordingly methods for diagnosing and monitoring these conditions are included within the scope of the present invention.

Accordingly, a test kit may be prepared for the demonstration of the presence and activity of AGEs, comprising:

(a) a predetermined amount of at least one labeled immunochemically reactive component obtained by the direct or indirect attachment of an advanced glycoslation endproduct or a specific binding partner thereto, to a detectable label;

(b) other reagents; and (c) directions for use of said kit.

More specifically, the diagnostic test kit may comprise:

(a) a known amount of a binding partner to an advanced glycosylation endproduct as described above, or a ligand thereof, generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may comprise:

(a) a labeled component which has been obtained by coupling the binding partner of the advanced glycosylation endproduct to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the advanced glycosylation endproduct and a specific binding partner thereto.

In the embodiment of the invention wherein antibodies to AGEs are to be used as the binding partner, such antibodies can for example, be produced and isolated by standard methods including the well known hybridoma techniques.

The existence of antibodies against advanced glycosylation endproducts makes possible another method for isolating other AGEs and their ligands. The method takes advantage of an antibody characteristic known as idiotypy. Each antibody contains a unique region that is specific for an antigen. This region is called the idiotype. Antibodies themselves contain antigenic determinants; the idiotype of an antibody is an antigenic determinant unique to that molecule. By immunizing an organism with antibodies, one can raise "anti-antibodies" that recognize them, including antibodies that recognize the idiotype. Antibodies that recognize the idiotype of another antibody are called anti-idiotype antibodies. Some anti-idiotypic antibodies mimic the shape of the original antigen that the antibody recognizes and are said to bear the "internal image" of the antigen. (Kennedy, 1986.) When the antigen is a ligand, certain anti-idiotypes that bind to that ligand's receptor. Investigators have identified several of these, including anti-idiotypes that bind to receptors for insulin, angiotensin II, adenosine I, β-adrenalin, and rat brain nicotine and opiate receptors. (Carlsson and Glad, 1989).

Taking advantage of this phenomenon, other ligands may be isolated using anti-idiotypic antibodies. Anti-idiotypes may be used to screen for molecules binding to the original antigen.

As stated earlier, the mesangial cell receptors and/or its proteins may be prepared by isolation and purification from MCs known to bear or produce the receptors and/or its proteins. The cells or active fragments likely to participate in receptor protein synthesis or to have receptor protein associated therewith may be subjected to a series of known isolation techniques, such as for example elution of detergent-solubilized rat MC membrane proteins from an AGE-protein affinity matrix, whereupon the present receptor proteins may be recovered. A specific protocol is set forth by way of illustration in the examples. The present invention naturally contemplates alternate means for preparation of the component proteins, including stimulation of receptor producer cells with promoters of receptor synthesis followed by the isolation and recovery of the receptor as indicated above, as well as chemical synthesis, and the invention is accordingly intended to cover such alternate preparations within its scope.

The present invention also extends to antibodies including polyclonal and monoclonal antibodies, to the receptor proteins that would find use in a variety of diagnostic and therapeutic applications. For example, the antibodies could be used to screen expression libraries to obtain the gene that encodes either the receptor complex or its component proteins. Further, those antibodies that neutralize receptor activity could initially be employed in intact animals to better elucidate the biological role that the receptor plays. Such antibodies could also participate in drug screening assays to identify alternative drugs or other agents that may exhibit the same activity as the receptor proteins.

Both polyclonal and monoclonal antibodies to the receptor proteins proteins are contemplated, the latter capable of preparation by well known techniques such as the hybridoma technique, utilizing, for example, fused mouse spleen lymphocytes and myeloma cells. Immortal, antibody-producing cell lines can also be created by techniques other than fusion, such as direct transformation of B lymphocytes with oncogenic DNA, or transfection with Epstein-Barr virus. Specific polyclonal antibodies can be raised. Naturally, these antibodies are merely illustrative of antibody preparations that may be made in accordance with the present invention.

As the receptor proteins appear to play a role in the recognition and removal of advanced glycosylation endproducts in vivo, the present invention contemplates both diagnostic and therapeutic applications for these agents. Accordingly, the receptor proteins may be prepared for use in a variety of diagnostic methods, set forth in detail hereinafter, and may be labeled or unlabeled as appropriate. Likewise, the MC receptor proteins may be prepared for administration in various scenarios for therapeutic purposes, in most instances to assist in reducing the concentration of AGEs in vivo.

The receptor proteins may be prepared in a therapeutically effective concentration as a pharmaceutical composition with a pharmaceutically acceptable carrier. Other compatible pharmaceutical agents may possibly be included, so that for example certain agents may be simultaneously coadministered. Also, the receptor proteins may be associated with or expressed by a compatible cellular colony, and the resulting cellular mass may then be treated as a therapeutic agent and administered to a patient in accordance with a predetermined protocol. Numerous therapeutic formulations are possible and the present invention contemplates all such variations within its scope. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, catheterizations and the like.

Corresponding therapeutic utilities take advantage of the demonstrated activity of the present receptor complex and/or the component proteins toward advanced glycosylation endproducts. Thus, to the extent that the in vivo recognition and removal of AGEs serves to treat ailments attributable to their presence in an excess concentration, the administration of the present receptor complex and/or the component proteins comprises an effective therapeutic method. Such conditions as diabetic nephropathy, renal failure and the like may be treated and/or averted by the practice of the therapeutic methods of the present invention. Average quantities of the active agent may vary and in particular should be based upon the recommendations and prescription of a qualified physician or veterinarian, with an exemplary dosage regimen extending to up to about 25 mg/kg/day.

The present invention also relates to a variety of diagnostic applications, including methods for the measurement of the presence and amount of advanced glycosylation endproducts in both plants and animals, including humans. The methods comprise assays involving in addition to the analyte, one or more binding partners of the advanced glycosylation endproducts, and one or more ligands.

The present invention will be better understood from a consideration of the following illustrative examples and data. Accordingly, Examples I and II presented in parent application Ser. No. 453,958 confirm the basic hypothesis that the in vivo recognition and removal of AGEs is receptor mediated, and Examples III presents the investigations and experiments that have resulted in the identification of the mesangial cell-derived AGE receptors of the present invention.

EXAMPLE 1

In this example, the existence of the receptor-mediated clearance system of advanced glycosylation endproducts that underlies the present assay was initially explored, in part, by the performance of a competitive phagocytosis assay was conducted with whole monocytes. A full review of the details of the experimental procedures involved is presented in U.S. Pat. No. 4,900,747, and reference may be made thereto for such purpose.

In this example, human red blood cells (RBCs) were collected and isolated, and separate quantities were prepared to facilitate the performance of the assay. Specifically, a quantity of RBCs were opsonized by incubation with an appropriate antiserum. A further quantity was bound to the advanced glycosylation endproduct FFI by a carbodiimide bond, and additional RBCs were separately glycosylated by reactions with glucose, glucose-6-phosphate, xylose and arabinose, respectively. Lastly, AGE-BSA and human monocytes were prepared. Phagocytosis assays proceeded by the incubation of the RBCs with the monocyte cultures followed by fixation of the sample wells and lastly counting under 40x phase microscopy.

An FFI-RBC half life assay was also conducted with Balb/c mice that were inoculated with FFI-RBC suspensions labeled with $^{51}Cr$. The labeled cells were washed at least four times to remove unbound isotope. Twelve Balb/c mice were then injected intravenously with 200 $\mu l$ RBC suspension. Each sample was administered in three Balb/c mice. At appropriate time intervals the mice were bled (0.2 ml) and radioactivity levels were measured by counting.

RESULTS

Maximum binding of red cells was observed on Day-7 of monocyte incubation in vitro. Maximum binding and endocytosis of FFI-RBC was complete within 30-45 minutes while opsonized cells were maximally bound within 15 minutes. At the end of one hour incubation of FFI-coupled RBC's with cultured human monocytes, per cent phagocytosis and phagocytic index were estimated. As shown in FIG. 1, % erythrophagocytosis of FFI-modified red cells (55%) and IgG-coated red cells (70%) were significantly higher than that of control PBS-treated cells (4%). Similarly the phagocytic index of FFI-treated RBC's was greatly elevated (3.4) as compared to normal controls (1.2).

Figure 2:
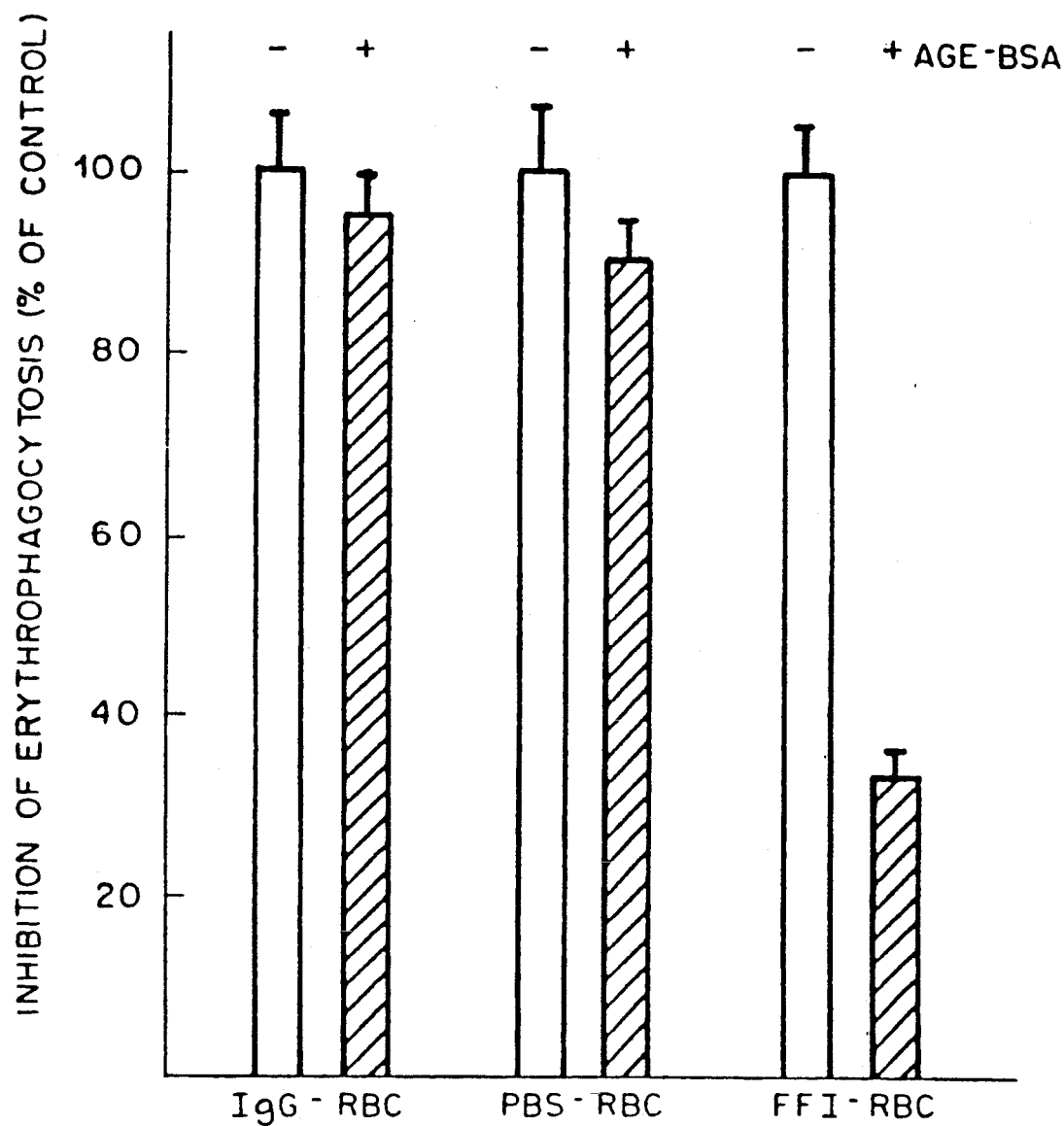
FIG. 2 is a graph illustrating an assay in accordance with the present invention by the competitive inhibition in red blood cell binding caused by the introduction into a sample of an agent capable of stimulating red blood cells to increase their activity of recognition and removal of advanced glycosylation endproducts.
Figure 3:
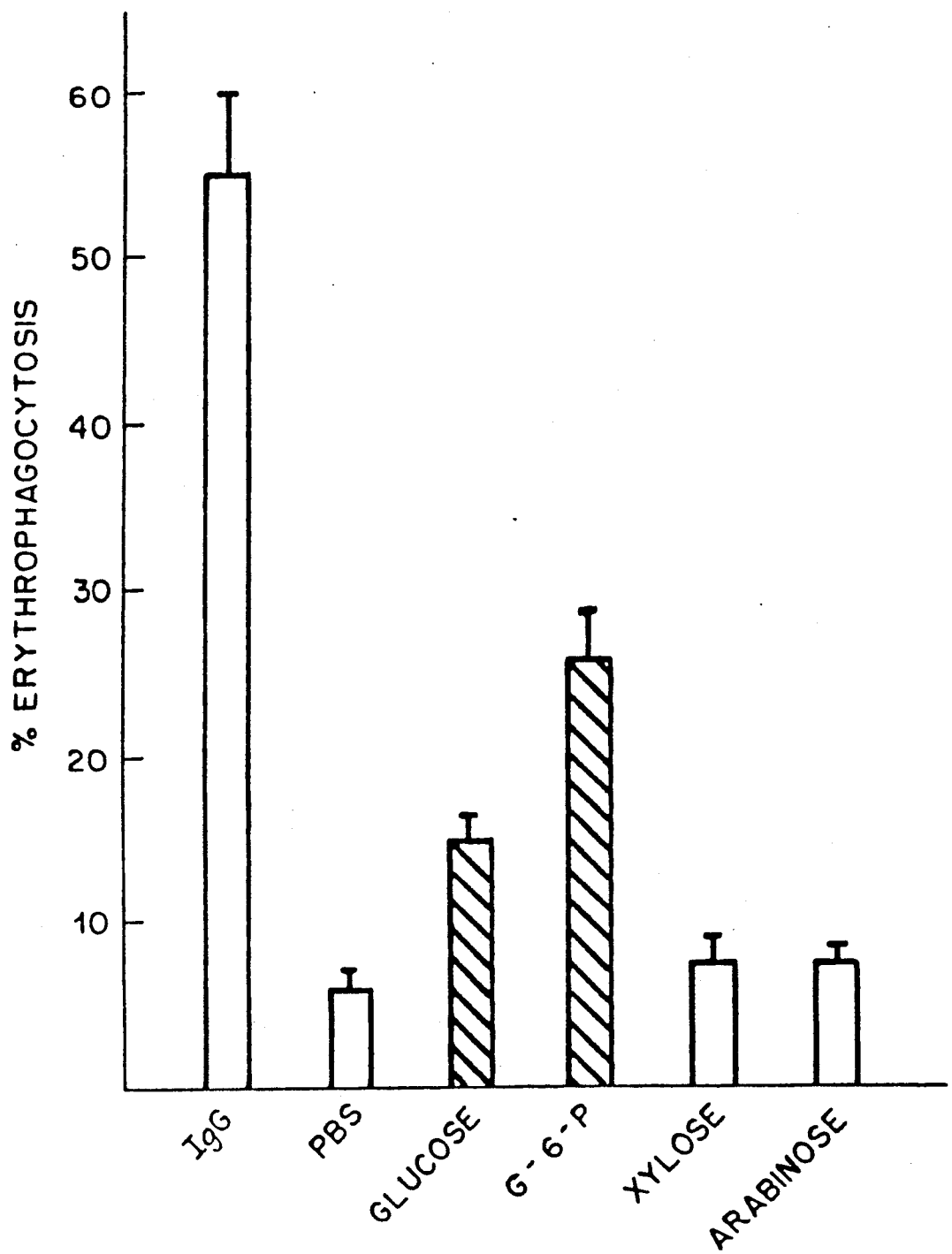
FIG. 3 is a bar graph illustrating the comparative uptake and degradation of advanced glycosylation endproducts by mouse macrophages exposed to various stimulator compounds.

In order to establish the specificity of the interaction of FFI-RBC's with the human monocytes, competition experiments were carried out in which binding and ingestion of red cells was observed in the absence and presence of AGE-BSA, prepared as described in Methods (Vlassara et al., supra.). As shown in FIG. 2, the addition of AGE-BSA at concentrations of 500 µg/ml inhibited the FFI-RBC binding by more than 70% of the control. In contrast, AGE-BSA did not inhibit opsonized or PBS-treated red cells, even at maximal concentrations (1 mg/ml). These data suggested that FFI-modified red cells were recognized and bound specifically by the monocyte AGE-binding site, and consequently confirmed the operability of the present assay.

DISCUSSION

The above tests extend previous observations on the recognition of advanced glycosylation endproducts (AGE) by a specific monocyte/macrophage receptor, and present evidence that such adducts once attached chemically or formed in vitro on the surface of intact human cells can induce cell binding and ingestion by normal human monocytes. The experiments establish the development of a competitive receptor-based assay for AGEs measuring by way of illustration herein, AGE-red cell binding in the presence of large excess of AGE-BSA (Vlassara et al., supra.).

EXAMPLE 2

This example comprises a series of experiments that were initially performed to measure the ability of agents to stimulate phagocytic cells to stimulate uptake and degradation of endproducts (AGEs), and thereby further confirmed the hypothesis that this activity is receptor-mediated.

Several AGEs were prepared using the same procedure as disclosed in Example 1, above. Accordingly, FFI-HA was prepared as described and quantities were bound to both human and bovine albumin. A water soluble carbodiimide was used to attach the acid moiety of the FFI-HA to an amino group on the protein. After preparation, the conjugate was purified and then used in vitro to stimulate macrophages, by incubation for from 4 to 24 hours.

The AGEs that were to be observed for uptake and degradation were appropriately radiolabeled so that they could be traced. Thereafter, the stimulated macrophages were tested by exposure to the radiolabeled AGEs following exposure to various agents to measure the effect that these agents had on the ability of the macrophages to take up and degrade the labeled AGEs. The above procedures conform to the protocol employed by Vlassara et al., supra, and confirmed that a competitive assay based on a cellular receptor for AGEs is feasible.

Figure 4:
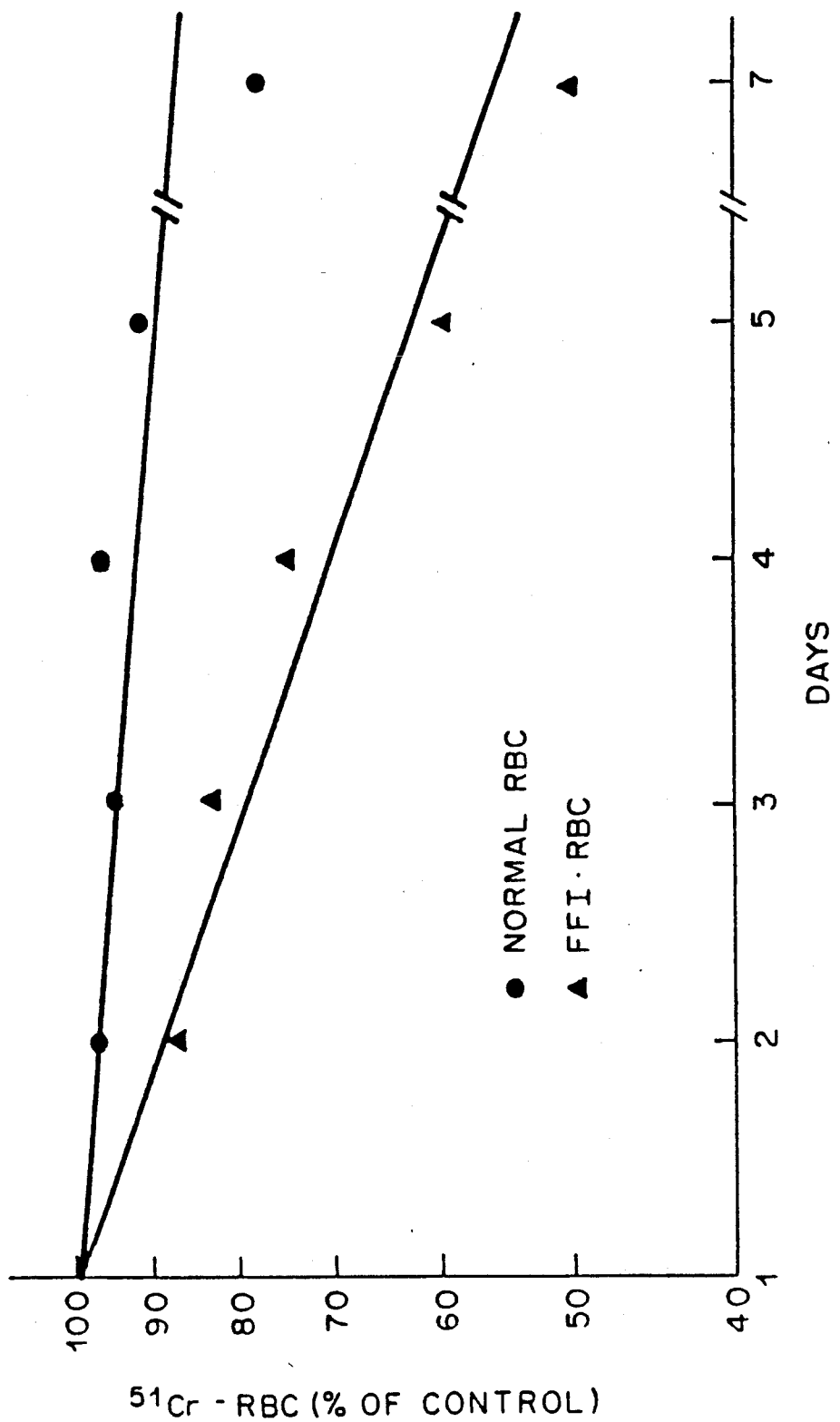
FIG. 4 is a bar graph illustrating data similar to that set forth in FIG. 3, with respect to one day old human monocytes.

It was also demonstrated that monocyte or macrophage cells can also be stimulated by AGE-carrier molecules which result in cells with enhanced ability to bind, internalize and degrade other AGE-molecules. AGE-carrier molecules are made, for example, from the reaction of glucose or glucose-6-phosphate with albumin. After purification of the reaction product, the AGE-albumin uptake of AGE-macromolecules demonstrated as in (A) above. AGE-BSA (prepared from the incubation of glucose-6-phosphate with albumin for 6-8 weeks) at 0.1 mg/ml demostrates a stimulatory effect on AGE-BSA uptake by human monocytes (FIG. 4, bar AA), and shows a slight stimulation at higher concentrations (bars BB and CC). This observation further supports the role of these ligands in conjunction with cellular receptors and point to the application of these agents in a competitive AGE assay protocol.

EXAMPLE 3

Materials and Methods

Cell culture: Primary cultures of rat MCs were obtained from outgrowths of isolated rat glomeruli by Dr. M. Ganz (Yale University, N.Haven). In brief, rats were anesthetized with ether and the kidneys were excised under sterile conditions. After removing the kidney capsule, the kidney cortices were isolated, minced to a fine paste with a razor blade, and then pressed through serial stainless steel sieves (Tyler USA No. 140, 80, and 200). Glomeruli were collected from the top of the 75 micrometer sieve. This process resulted in >98% pure glomeruli. The glomeruli were then pelleted and resuspended in DMEM supplemented with 20% FBS, 5 µg/ml bovine insulin, 2 mM L-glutamine, and 40 µg/ml gentamicin. The glomerular suspensions were plated onto tissue culture flasks and incubated at 37° C. in 5% $CO_2$. Primary cultures were allowed to grow for 3-4 weeks at which time the MCs were confluent. MCs were used between the fourth and ninth passages.

The purity of the rat MC populations was documented. The MCs exhibited a uniform straplike appearance and stained positively for Thy 1—1 antigen, myosin and actin. They were sensitive to mitomycin C, a MC toxin, but were resistant to the aminonucleoside puromycin, an epithelial cell toxin. Fibroblast contamination was excluded by demonstrating the ability of the cells to grow in media in which L-valine had been substituted for D-valine. In addition, they stained negative for factor VIII and cytokeratin. Over the experimental period they continued to maintain a uniform stellate appearance.

Human MC were provided by Dr. J. Floege and Dr. K. Resch, (Hannover, FRG). In brief, normal human kidney tissue was obtained from nephrectomy specimens. Renal cortices were homogenized and glomeruli were isolated following passage through a series of graded sieves. The glomeruli were then treated with bacterial collagenase (Worthington Biochemical Corporation, Freehold, N.J.) at 37° C. for 30 minutes, and after extensive washing the glomerular remnants were plated onto tissue culture flasks in RPMI 1640, supplemented with 20% FBS, 2 mM L-glutamine, 2 mM sodium pyruvate, 5 µg/ml bovine insulin, 5 µg/ml human transferrin, 1% (v/v) non-essential amino acids, and gentamicin. Cellular outgrowths appeared between days 5-8, and all experiments were performed using cells between the fourth and tenth passage.

The purity of the MC population was demonstrated. In brief, immunofluorescent staining demonstrated prominent intracellular staining for smooth muscle cell myosin, MHC class I antigen, vimentin, collagen IV, and fibronectin. The cells stained negative for Fc-receptor, MHC II surface antigen, cytokeratin and factor VIII, and were able to grow in D-valine substituted medium.

Preparation of ligands: AGE- bovine serum albumin (BSA) and AGE-ribonuclease were made by incubating BSA and bovine ribonuclease (Sigma Chemical Co, St. Louis, Mo.) with 0.5M glucose-6-phosphate (G6P), at 37° C. for 4 to 6 weeks in a 10 mM PBS buffer, pH 7.4, in the presence of protease inhibitors and antibiotics. Unincorporated glucose was removed by dialysis against 1X PBS. The concentration of AGE-BSA was determined and the concentration of ribonuclease was determined spectrophotometrically.

AGE formed on either BSA or ribonuclease was assessed based on characteristic absorption and fluorescence spectra (emission at 450 nm, excitation at 390 nm) and quantitated by a radioreceptor assay using intact RAW 264.7 cells grown in 96-well plates. According to this assay, AGE-BSA contained approximately 70 AGE U/mg (one unit of AGE is defined as the concentration of unknown agent required to produce 50% inhibition of standard $^{125}$I-AGE-BSA binding) and AGE-ribonuclease contained 62 AGE U/mg.

Borohydride Reduction: To examine the effect of early glycosylation product reduction on ligand binding, AGE-BSA was incubated with 200 molar excess $NaBH_4$ (Sigma Chemical Co) for 10 minutes at 4° C., followed by 1 hour at room temperature. The reduced AGE-BSA was then dialyzed against 1X PBS and the protein concentration was determined as above. The chemically defined AGE, 2-furoyl-4(5)-2-furanyl-1-H-imidazole (FFI-HA), was synthesized and linked to BSA with 100 mM water soluble carbodiimide.

Iodination of AGE-BSA: AGE-BSA was iodinated with carrier-free-$^{125}$I by the IODO-GEN method (Bio-Rad) of Fraker and Speck. Samples were dialyzed against PBS until >95% of radioactivity was trichloroacetic acid (TCA)-precipitable and the samples were iodide free.

Preparation of AGE-matrices: 6-well plates coated with rat tail collagen, type I, human fibronectin, and polylysine were purchased from Collaborative Research, Inc. (Bedford, Mass.). AGE-matrices were produced by incubating the various matrix coated plates in 0.5M G6P, at 37° C. for 2-3 weeks in 10 mM PBS buffer (pH 7.4), as described for AGE-BSA. Control matrices were incubated under identical conditions in buffer alone. Following incubation, the plates were washed extensively with 1X PBS. The amount of adhered collagen I was determined using a hydroxyproline assay, while adhered fibronectin and laminin were determined by the method of Lowry et al. after dissolving the matrix in 2N NaOH at 37° C. overnight, as described by Jones et al., and by absorbance at 280 nm. In both cases similar amounts of unmodified or AGE-modified matrix proteins adhered (collagen I, ~85%; fibronectin, ~70%; laminin, ~80% of the plated amount remained attached to the plates). AGE levels in matrix proteins were quantitated by an AGE-specific radioreceptor assay, as described above. AGE-collagen I contained 47 AGE U/mg, AGE-fibronectin 54 AGE U/mg and AGE-laminin, 51 U/mg. Unmodified matrices contained less than 5 AGE U/mg protein.

Membrane preparation: Rat and human MCs were grown to confluency in 150 mm petri dishes. Cells were detached from the plates by PBS containing 3% EDTA and protease inhibitors (2 mM phenylmethylsulfonylfluoride [PMSF], 10 μg/ml aprotinin, 5 ng/ml pepstatin, and 1 mM 1,10-phenanthroline).

Following centrifugation, cells were disrupted with a tight Dounce homogenizer, pestle A, in a solution of PBS, with 10 mM EDTA and protease inhibitors, as stated above. The nuclear and organelle-enriched fraction were removed by centrifugation at 13,000×g. Membranes were then isolated from the supernatant by centrifugation at 100,000×g for 1 hour at 4° C. The resulting enriched membrane fraction was solubilized in PBS, containing 1% triton X-100, and 2 mM PMSF. The protein concentration was determined. This material was then used for binding and ligand blotting studies.

Binding studies: Filter binding studies were performed according to the method of Schneider et al. and Daniel et al. with minor modifications. 10-20 μg of MC membrane protein was dot-blotted onto nitrocellulose filters. The nitrocellulose filters were then cut and each dot was placed in a separate well of a 24-well plate. Following blocking of the filters for 1 hour at 4° C. in PBS containing 1.5% BSA, binding studies were initiated by adding various concentrations of radioactive ligand to the individual wells.

At 2 hours, the nitrocellulose filters were washed 3 times with ice-cold 1X PBS, and radioactivity bound was quantitated using a Packard Tricarb Scintillation counter.

Specific binding was defined as the difference between total binding (radioligand incubated with membrane protein alone), and nonspecific binding (cells incubated with radiolabelled ligand plus 100-fold excess unlabelled ligand). Scatchard analysis of the data was performed to determine the binding affinity constant and the receptor number. Competition studies were performed in a similar manner to the binding studies, with the exception that the nitrocellulose filters were preincubated with the competitor for 1 hour before adding the radiolabelled ligand.

Binding studies were also performed on confluent MCs in 6-well plates. The studies were performed in 1 ml of RPMI-1640 at 4° C. following the addition of various concentrations of radioactive ligand. After 2 hours of binding, the radioligand-containing medium was removed, and the cells were washed with ice-cold PBS. The cell monolayer was then disrupted with 1% triton X-100, and the cell-associated radioactivity was quantitated. Protein concentration was determined by the method of Bradford. Specific binding was determined in an identical manner to that described above for the filter binding assay.

Ligand blotting: MC membrane preparations (5 ug aliquots) were electrophoresed on a nonreducing SDS-PAGE (10%), and then electroblotted onto a nitrocellulose filter. Following blocking for 1 hour in a solution of PBS containing 1.5% BSA, the nitrocellulose filter was probed with $^{125}$I- AGE-BSA in the presence of 100-fold excess of either BSA or AGE-BSA. The blot was washed 3 times with 1X PBS and exposed to Kodak XAR-5 film at −80° C.

Uptake and degradation: MC uptake and degradation was performed with a minor modification of previously described procedures. Briefly, MCs were grown to confluency in 6-well plates in DMEM containing 20% FBS and insulin. MC accumulation of radioactive ligand (AGE-BSA) was assessed by incubating cells with various concentrations of $^{125}$I-AGE-BSA, in the presence and absence of 100-fold excess of unlabelled AGE-BSA, for 4 hours at 37° C . After washing the cells 3 times with ice-cold PBS, the cells were solubilized in 1% Triton X-100 for 45 minutes at room temperature, and the amount of cell associated radioactivity was determined. Specific uptake was defined by the same criteria as used for the MC binding studies. Protein concentration was determined by the method of Bradford. Degradation was determined by measuring TCA-soluble radioactivity in the aspirated medium.

Proliferation assays: Rat MCs in DMEM containing 20% FBS were plated at $1 \times 10^4$ cells/well onto flat-bottom 96-well microtitre plates, which had been pre-coated with different amounts of either AGE-modified or unmodified matrix proteins. 24 hours later, the cells were washed with 1X PBS and incubated for an additional 48 hrs in medium containing 0.3% FBS. The cells were then labelled with 2 uCi of ($^3$H) thymidine (Amersham Corp., Arlington Heights, Ill.) for 18–24 hours, following which the supernatants were aspirated and the cells in each well were harvested onto glass fiber filters with an automated cell harvester. The amount of ($^3$H) thymidine incorporated was determined with a Beckman Scintillation Counter.

To confirm thymidine incorporation data, parallel studies were carried out using an immunocytochemical assay system for detection of DNA synthesis by measuring bromodeoxyuridine (BrdU) incorporation, while in separate experiments cells were trypsinized and counted in a Coulter particle counter. The data obtained by these two additional methods were consistent with $^3$H-thymidine results (variations between replicate wells deviated no more than 10%).

Fibronectin production: Human MCs in RPMI-1640 medium supplemented with 20% FBS were plated at $2 \times 10^5$ cells per well onto 6-well plates which had been coated with glucose-modified or unmodified matrix proteins. After 24 hours, the cells were washed with 1X PBS and incubated in medium containing 0.3% FBS for 48 hours. The cells were then labeled in methionine free medium for 3 hours with 200 uCi of (35S) methionine and cysteine (Translabel, ICN).

After labeling, the medium was removed and the cell monolayers were washed with cold 1X PBS. The monolayers were extracted with 0.5 ml of a 1M urea solution containing 1 mM dithiothreitol (DTT), 10 mM Tris-HCL (pH) 7.4), 10 mM EDTA, and 2 mM PMSF.

Fibronectin was then isolated from the medium and matrix by immunoprecipitation with an IgG purified anti-human fibronectin antibody (Cappel, Malvern, Pa.). Anti-fibronectin antibody was added to the samples and incubated overnight at 4° C. To insure than any differences in fibronectin synthesis were not due to different number of cells/well, equal amounts of TCA-precipitable counts were immunoprecipitated from each well. The immune complexes were isolated using protein A-Sepharose beads (Pharmacia).

After washing the protein A-Sepharose beads 3 times in 100 mM Tris HCl (pH 7.4), 0.5% SDS, 0.5% Triton X-100, 2 mM PMSF, and 10 mM EDTA, fibronectin was released by heating at 100° C. for 5 minutes in SDS-PAGE sample buffer, and analyzed by gel electrophoresis and fluorography. The amount of fibronectin from each sample was quantitated by slicing the fibronectin band from the gel and determining (35S) methionine and cysteine incorporation in a liquid scintillation counter.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for measuring the presence of advanced glycosylation endproducts in a biological sample comprising the steps of:
    A. preparing at least one biological sample suspected of containing said advanced glycosylation endproducts;
    B. preparing at least one corresponding binding partner directed to said samples, said binding partner comprising at least one receptor protein for said advanced glycosylation endproducts derived from the mammalian mesangial cells, said receptor comprising at least one receptor protein reactive with AGEs, characterized as follows:
        (a) it has a molecular mass from 30 to 50 kD;
        (b) it is reactive with AGE-BSA, AGE-RNAse, AGE-collagen I and AGE-BSA reduced with NaBH$_4$ and has a binding affinity of $2.0 \pm 0.4 \times 10^{-6} M^{-1}$ (kD = 500 nM);
        (c) it is non-reactive with BSA, collagen I, RNAse or chemically synthesized FFI-BSA; and
        (d) it is present on mesangial cell membranes prior to purification;
    C. placing a detectable label on a material selected from the group consisting of said sample, a ligand to said binding partner and said binding partner;
    D. placing the labeled material from Step C in contact with a material selected from the group consisting of the material from Step C that is not labeled; and
    E. examining the resulting sample of Step D for the extent of binding of said labeled material to said unlabeled material.

2. The method of claim 1 wherein said sample is selected from the group consisting of plant matter; blood; plasma; urine; cerebrospinal fluid; lymphatic fluid; tissue; a product of the reaction between protein and a sugar; a product of the reaction between DNA and a sugar, and mixtures thereof.

3. The method of claim 1 wherein said advanced glycosylation endproduct is an amino group containing compound selected from the group consisting of substituted and unsubstituted amino acids, substituted and unsubstituted proteins, and substituted and unsubstituted amino acid-containing biopolymers.

4. The method of claim 3 wherein said advanced glycosylation endproduct is a glucose residue-bearing compound selected from the group consisting of proteins, biopolymers and mixtures thereof.

5. The method of claim 1 wherein said binding partner is selected from the group consisting of mammalian mesangial cells containing receptors for advanced glycosylation endproducts, mammalian mesangial cell membranes containing receptors for advanced glycosylation endproducts, and cell proteins derived from mammalian mesangial cell membranes that comprise receptors for advanced glycosylation endproducts.

6. The method of claim 1 wherein a detectable label selected from the group consisting of enzymes, chemicals which floresce and radioactive elements is placed on a member selected from the group consisting of said binding partner and said ligand.

7. The method of claim 6 wherein the label is an enzyme selected from the group consisting of peroxidase, β-glucuronidase, β-D-glucosidase, β-D-galactosidase, urease, glucose oxidase plus peroxidase, galactose oxidase plus peroxidase, hexokinase plus GPDase, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase.

8. The method of claim 6 wherein the label is a chemical which floresces selected from the group consisting of fluorescein, rhodamine, and auramine 9. The method of claim 6 wherein the label is a radioactive element selected from the group consisting of $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}H$, and $^{186}Re$.

10. An in vitro method for monitoring the course and efficacy of a drug or dietary therapy in which an alteration in the presence and amount of advanced glycosylation endproducts is implicated comprising performing the method of claim 1.

11. A method for determining the amount of advanced glycosylation endproducts in an analyte comprising:
A. exposing AGE receptors derived from mesangial cells to a sample of said analyte and blotting onto a suitable carrier or substrate, said AGE receptors comprising at least one receptor protein reactive with AGEs, characterized as follows:
  (a) it has a molecular mass from 30 to 50 kD;
  (b) it is reactive with AGE-BSA, AGE-RNAse, AGE-collagen I and AGE-BSA reduced with NaBH$_4$ and has a binding affinity of $2.0 \pm 0.4 \times 10^{-6} M^{-1}$ (kD = 500 nM);
  (c) it is non-reactive with BSA, collagen I, RNAse or chemically synthesized FFI-BSA; and
  (d) it is present on mesangial cell membranes prior to purification;
B. incubating the sample after preparation in accordance with Step A, in a blocking buffer;
C. applying a quantity of $^{125}I$-AGE-BSA to the sample of Step B with removal of any excess by rinsing; and
D. measuring the amount of said advanced glycosylation endproduct bound to said analyte by detecting the radioactivity of the sample of Step C.

12. A method for determining the amount of advanced glycosylation endproducts in an analyte comprising:
A. providing a sample of mammalian mesangial cells, mammalian menangial cell membranes containing AGE receptors or AGE receptor proteins, said AGE receptors comprising at least one receptor protein reactive with AGEs, characterized as follows:
  (a) it has a molecular mass from 30 to 50 kD;
  (b) it is reactive with AGE-BSA, AGE-RNAse, AGE-collagen I and AGE-BSA reduced with NaBH$_4$ and has a binding affinity of $2.0 \pm 0.4 \times 10^{-6} M^{-1}$ (kD = 500 nM);
  (c) it is non-reactive with BSA, collagen I, RNAse or chemically synthesized FFI-BSA; and
  (d) it is present on mesangial cell membranes prior to purification;
B. inoculating said sample with an analyte and a labelled known advanced glycosylation endproduct; and
C. counting the amount of label that is bound to and/or internalized by said sample.

13. The method of claim 12 wherein said analyte is selected from the group consisting of the solubilized collagen extract from arterial walls, serum and urine.

14. The method of claim 12 wherein plural analyte samples are taken from normal subjects and subjects suspected of suffering from diabetes, the results of the measurement of advanced glycosylation endproduct content of said samples are compared, and such comparison yields a determination of the presence and extent of such diabetic condition.

15. The method of claim 12 wherein said sample is a cell protein selected from the group consisting of a 90 kD protein derived from RAW 264.7 cells, a 40 kD protein derived from RAW 264.7 cells, and a 30-35 kD protein derived from rat liver membranes, a 60 kD protein derived from rat liver membranes, a 50 kD protein derived from human and/or rat mesangial cells, a 40 kD protein derived from human and/or rat mesangial cells, a 30-35 kD protein derived from human and/or rat mesangial cells, an IgE binding protein from mammalian cells, and mixtures thereof.

16. A method for determining the amount of advanced glycosylation endproducts in an analyte comprising:
A. preparing a sample of said analyte bound to a substrate;
B applying to the sample of Step A a quantity of a ligand derived from mesangial cells bearing a known advanced glycosylation endproduct;
C. applying to the sample of Step B a quantity of an anti-serum to advanced glycosylation endproducts;
D. measuring the amount of said advanced glycosylation endproduct bound to said analyte by detecting the quantity of antiserum present on the bound substrate sample of step C; and
E. wherein mesangial cells define at least one receptor for AGE's, said receptor for AGEs in turn comprising at least one receptor protein reactive with AGEs, characterized as follows:
  (a) it has a molecular mass from 30 to 50 kD;
  (b) it is reactive with AGE-BSA, AGE-RNAse, AGE-collagen I and AGE-BSA reduced with NaBH$_4$ and has a binding affinity of $2.0 \pm 0.4 \times 10^{-6} M^{-1}$ (kD = 500 nM);
  (c) it is non-reactive with BSA, collagen I, RNAse or chemically synthesized FFI-BSA; and
  (d) it is present on mesangial cell membranes prior to purification.

17. A test kit for measuring the presence of advanced glycosylation endproducts in analytes, comprising:
A. a predetermined amount of at least one labeled immunochemically reactive component obtained by the direct or indirect attachment of binding partners to advanced glycosylation endproducts, ligands reactive with said advanced glycosylation endproducts, ligands reactive with said binding partners, or specific binding partners thereto, to a detectable label, at least one of said binding partners to advanced glycosylation endproducts, ligands or specific binding partners containing AGE receptors being derived from mammalian mesangial cells, wherein said mesangial cells define at least one receptor for AGEs, said receptor for AGEs in turn comprising at least one receptor protein reactive with AGEs, characterized as follows:
  (a) it has a molecular mass from 30 to 50 kD;

(b) it is reactive with AGE-BSA, AGE-RNAse, AGE-collagen I and AGE-BSA reduced with NaBH$_4$ and has a binding affinity of $2.0\pm0.4\times10^{-6}M^{-1}$ (kD=500 nM);

(c) it is non-reactive with BSA, collagen I, RNAse or chemically synthesized FFI-BSA; and (d) it is present on mesangial cell membranes prior to purification;

B. other reagents; and

C. directions for use of said kit.

18. The test kit of claim 17 wherein said analyte is selected from the group consisting of plant matter; blood; plasma; urine; cerebrospinal fluid; lymphatic fluid; tissue; the fluorescent chromophore 2-(2-furoyl)-4(5)-(2-furanyl)-1H-imidazole; a product of the reaction between protein and a sugar; a product of the reaction between DNA and a sugar; and mixtures thereof.

19. The test kit of claim 17 wherein said analyte is an amino-group containing compound is selected from the group consisting of substituted and unsubstituted amino acids, substituted and unsubstituted proteins, and substituted and unsubstituted amino acid-containing biopolymers.

20. The test kit of claim 19 wherein said amino-group containing compound is selected from the group consisting of 6-aminohexanoic acid, methylamine, poly-L-lysine, α-t-BOC-lysine, albumin, collagen, DNA, and glucose residue-bearing compounds where said glucose residues are replaced by the residues of another reducing sugar.

21. The test kit of claim 20 wherein said glucose residue-bearing compounds are selected from the group consisting of proteins, biopolymers and mixtures thereof.

22. The test kit of claim 17 wherein said binding partner is selected from the group consisting of mammalian mesangial cells defining receptors for advanced glycosylation endproducts, mesangial cell components defining receptors for advanced glycosylation endproducts, and mesangial cell proteins comprising receptors for advanced glycosylation endproducts.

23. The test kit of claim 22 wherein said mesangial cell proteins are selected from the group consisting of a 50 kD protein derived from human and/or rat mesangial cells, a 40 kD protein derived from human and/or rat mesangial cells and a 30–35 kD protein derived from human and/or rat mesangial cells and mixtures thereof.

24. The test kit of claim 17 wherein said binding partner is an IgE binding protein selected from the group consisting of carbohydrate binding protein 35 (CPB-35), mouse lectin L-34, rat lung lectin RL-29, chicken skin lectin (CSL), bovine heart lectin (BHL), electric eel lectin (EEL), the macrophage lectin Mac-2, and recombinant rat IgE-binding protein (reBP).

25. The test kit of claim 17 wherein the label is an enzyme, a chemical that floresces, or a radioactive element.

26. The test kit of claim 25 wherein the enzyme is selected from the group consisting of peroxidase, β-glucuronidase, β-D-glucosidase, β-D-galactosidase, urease, glucose oxidase plus peroxidase, galactose oxidase plus peroxidase, hexokinase plus GPDase, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase.

27. The test kit of claim 25 wherein the label is a chemical that floresces selected from the group consisting of fluorescein, rhodamine, and auramine.

28. The test kit of claim 25 wherein the label is a radioactive element selected from the group consisting of $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

* * * * *